United States Patent [19]

Ottow et al.

[11] Patent Number: 5,478,956
[45] Date of Patent: Dec. 26, 1995

[54] 8-EN-19 11 β-BRIDGED STEROIDS, THEIR PRODUCTION AND PHARMACEUTICAL PREPARATIONS CONTAINING THEM

[75] Inventors: Eckhardt Ottow; Günter Neef; Walter Elger; Martin Schneider; Karl Fritzemeier, all of Berlin, Germany

[73] Assignee: Schering Aktiengesellschaft, Berlin, Germany

[21] Appl. No.: 66,018

[22] PCT Filed: Nov. 27, 1991

[86] PCT No.: PCT/EP91/02239

§ 371 Date: Sep. 28, 1993

§ 102(e) Date: Sep. 28, 1993

[87] PCT Pub. No.: WO92/09618

PCT Pub. Date: Jun. 11, 1992

[30] Foreign Application Priority Data

Nov. 27, 1990 [DE] Germany ............... 40 38 128.5

[51] Int. Cl.$^6$ .................. C07J 53/00; A61K 31/56
[52] U.S. Cl. ............... 552/510; 552/508; 552/544; 552/548; 552/553; 514/169; 514/172; 514/173; 514/175; 514/177; 514/178; 514/179
[58] Field of Search ............. 552/510, 508, 552/544, 548, 553; 549/265, 331; 514/169, 172, 173, 175, 177, 178, 179

[56] References Cited

U.S. PATENT DOCUMENTS

| | | | |
|---|---|---|---|
| 3,127,423 | 3/1964 | Fried et al. | 552/540 |
| 5,041,434 | 8/1991 | Liebkin | 514/182 |
| 5,095,129 | 3/1992 | Ottow et al. | 552/510 |
| 5,232,915 | 8/1993 | Ottow et al. | 514/63 |

FOREIGN PATENT DOCUMENTS

| | | |
|---|---|---|
| 0283428 | 9/1988 | European Pat. Off. . |
| 0360369 | 3/1990 | European Pat. Off. . |
| 3708942 | 9/1988 | Germany . |
| 3717169 | 12/1988 | Germany . |
| 3917274 | 11/1990 | Germany . |

*Primary Examiner*—Shean Wu
*Attorney, Agent, or Firm*—Millen, White, Zelano & Branigan

[57] ABSTRACT

8-En-19,11β-bridged steroids of general formula I

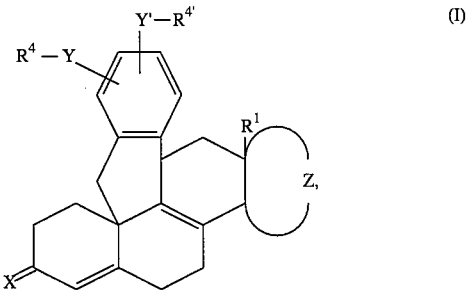

that have the 8,9-double bond as a new structural feature, and a process for their production are described. The substituents $R^1$ $R^4$-Y, $R^{4'}$-Y', X and Z have the meaning indicated in the description. The new compounds especially have at their disposal pronounced antigestagen effectivenss and are suitable for the production of pharmaceutical preparations.

20 Claims, No Drawings

8-EN-19 11 β -BRIDGED STEROIDS, THEIR PRODUCTION AND PHARMACEUTICAL PREPARATIONS CONTAINING THEM

This invention relates to the new 8-En-19,11β-bridged steroids, process for their production, pharmaceutical preparations containing these compounds, their use for the production of pharmaceutical agents as well as the new intermediate products necessary for this purpose.

The 8-En-19,11β-bridged steroids according to the invention are described by general formula I

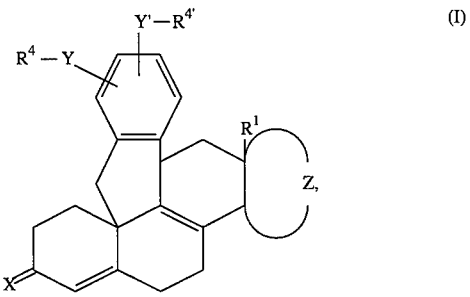

in which
R$^1$ stands for a methyl or ethyl radical,
X stands for an oxygen atom, a hydroxyimino group or two hydrogen atoms,
Z stands for the radical of a ring of formula

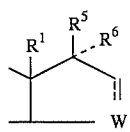

in which
R$^1$ has the meaning mentioned in formula I, the broken line starting from W means the possible presence of a double bond,
W means a CH$_2$, CH—, CH$_2$CH$_2$— or CHCH$_2$-radical,

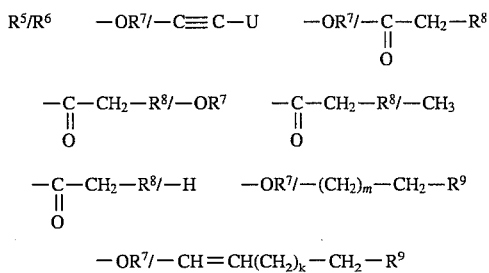

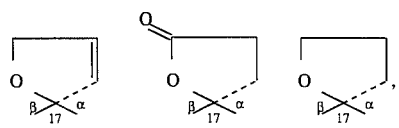

with R$^7$ meaning a hydrogen atom, an alkyl or acyl radical with 1 to 4 carbon atoms, U meaning a hydrogen atom, an alkyl, hydroxyalkyl, alkoxyalkyl, acyloxyalkyl group with 1 to 4 carbon atoms each in the alkyl or acyl radical or a halogen atom, R$^8$ means a hydrogen atom, a hydroxy group, an alkyl, O-alkyl or O-acyl group with 1 to 4 carbon atoms each,
R$^9$ means a hydrogen atom, a hydroxy or cyanide radical, an O-alkyl or O-acyl group with 1 to 4 carbon atoms each,
R$^{10}$ means a hydrogen atom, an alkyl or acyl group with 1 to 10 carbon atoms each,
m means 0, 1, 2 or 3,
k means 0, 1 or 2,
in which
R$^4$ and R$^{4'}$ are the same or different, respectively standing for a hydrogen atom, a cyanide radical an —OR$^{11}$—S(O)$_k$R$^{11}$, —N(O)$_n$R$^{12}$, —O—SO$_2$—R$^{13}$, —P(O)(OR$^{14}$)$_2$, —SiR$_3^{14}$ or —SnR$_3^{14}$ group with k meaning the numbers 0, 1 or 2, n meaning the numbers 0 or 1,
R$^{11}$ meaning a hydrogen atom or a C$_1$–C$_8$-alkyl radical,
R$^{12}$ meaning R$^{11}$, a cyanide or a C$_1$–C$_{10}$-acyl radical,
R$^{13}$ meaning a perfluorinated C$_1$–C$_4$-alkyl radical,
R$^{14}$ meaning a C$_1$–C$_4$-alkyl radical or
R$^{11}$ and R$^{12}$ within a —N(O)$_n$R$^{11}$R$^{12}$ group together, with the inclusion of N, form a 5 or 6 membered heterocyclic ring, and another heteroatom N, O or S can also be contained in the ring,
Y and Y' are the same or different, respectively mean an alkylene group with up to 20 carbon atoms having a direct bond, a straight-chain or branched, optionally double or triple bond(s), that is optionally substituted by one or more oxo-, C$_1$–C$_{10}$-acyloxy-, —OR$^{11}$, —S(O)$_k$R$^{11}$, and/or —N(O)$_n$R$^{11}$R$^{12}$ group(s) an optionally substituted carbocyclic or heterocyclic aryl radical or R$^4$—Y and R$^{4'}$—Y' together mean the radical of an optionally substituted saturated, unsaturated or aromatic 5 or 6 membered ring with 0 to 2 oxygen atoms, sulfur atoms and/or NR$^{11}$-groups, provided that k and n are greater than 0, only when R$^{11}$ stands for a C$_1$–C$_8$-alkyl radical,
and optionally their pharmaceutically compatible addition salts with acids.

Monosubstitution in 3, 4 or 5 position as well as disubstitution in 4 and 5 or 3 and 4 position with the formation of a fused second ring, for example a cyclohexene, pyrrole, furyl, pyrroline, 1,3-dioxacyclopentene, pyrazoline, didehydromorpholine, didehydropiperidine, didehydropiperazine, dihydropyrane, pyrimidine, pyridine, pyrazine, 1,4-dioxacyclohexene ring is preferred in the substitution of the phenyl ring.

The alkyl radicals standing for R$^1$ and R$^{11}$ should have, in the case of R$^1$, 1 or 2 carbon atoms, in the case of R$^{11}$, 1 to 8 carbon atoms and otherwise 1 to 4 carbon atoms, and the methyl, ethyl, propyl, isopropyl, butyl or methyl, ethyl, propyl groups are preferred.

If R$^{12}$ stands for an acyl radical, then a formyl, acetyl, propionyl, butyryl and benzoyl group is preferred.

R$^{11}$ and R$^{12}$ together with the inclusion of the nitrogen atom also stand for heterocyclic five or six ring, that in addition to N and C atoms can also additionally contain an O or S atom; for example the pyrrole, pyrrolidine, piperidine, piperazine, morpholine, oxa and thiazolidine as well as thiadiazolidine ring can be mentioned.

The alkyl, alkoxy as well as acyloxy groups contained in R$^5$ and R$^6$ or R$^7$, R$^8$, R$^9$, R$^{10}$ and U of general formula I should contain 1 to 4 carbon atoms each, and methyl, ethyl, propyl, isopropyl, methoxy, ethoxy, propoxy, isopropoxy, formyl, acetyl, propionyl and isopropionyl groups are preferred.

Of the alkenyl radicals in R$^6$ the propenyl and butenyl groups, that can be present in E or Z configuration, are preferred, i.e., if R$^6$ stands for —CH=CH(CH$_2$)$_k$CH$_2$—R$^9$, then k should preferably mean 0 or 1.

As optionally substituted carbocyclic or heterocyclic aryl radical a phenyl, naphthyl, 2-methoxyphenyl, 3-methoxyphenyl, 4-methoxyphenyl, 2-tolyl, 3-tolyl, 4-tolyl, 2-dimethylaminophenyl, 3-dimethylaminophenyl, 4-dimethylaminophenyl, furyl-2, furyl-3, thienyl-2, thienyl-3, pyridyl-2, pyridyl-3, pyridyl-4, pyrimidinyl, thiazolyl, imidazolyl radical can be suitable.

The following compounds are preferred according to the invention:

17β-hydroxy-11β,19-(4-methoxy-o-phenylene)-17α-(prop-1-inyl)-4,8-androstadien-3-one 11β,19-(4-ethylphenyl-o-phenylene)-17β-hydroxy-17α-(prop-1-inyl)-4,8-androstadien-3-one 11β,19-[4-(4-cyanophenyl)-o-phenylene]-17β-hydroxy-17α-(prop-1-inyl)-4,8-androstadien-3-one 11β, 19-[4-(4-cyanophenyl)-o-phenylene]-17α-(ethinyl)-17β-hydroxy-4,8-androstadien-3-one 11β,19-[4-(4-cyanophenyl)-o-phenylene]-17β-hydroxy-17α-(3-hydroxyprop-1-inyl)-4,8-androstadien-3-one 11β, 19-[4-(4-cyanophenyl)-o-phenylene]-17β-hydroxy-17α-(3-hydroxyprop-1(Z)-enyl)-4,8-androstadien-3-one 17β-hydroxy-17α-(prop-1-inyl)-11β, 19-[4-(5-pyrimidinyl)-o-phenylene]-4,8-androstadien-3-one 17β-hydroxy-17α-(3-hydroxyprop-1-inyl)-11β, 19-[4-(3-Pyridyl)-o-phenylene]-4,8-androstadien-3-one 17β-hydroxy-17α-(3-hydroxyprop-1-inyl)-11β, 19-[4-(4-methoxyphenyl)-o-phenylene]-4,8-androstadien-3-one 17β-hydroxy-17α-(3-hydroxyprop-1-inyl)-11β, 19-[4-(4-methylthiophenyl)-o-phenylene]-4,8-androstadien-3-one 11β, 19-(4-acetyl-o-phenylene)-17β-hydroxy-17α-(3-hydroxyprop-1-inyl)-4,8-androstadien-3-one 17β-hydroxy-17α-(3-hydroxyprop-1(Z)-enyl)-11β, 19-[4-(3-pyridyl)-o-phenylene]-4,8-androstadien-3-one 17β-hydroxy-17α-(3-hydroxyprop-1(Z)-enyl)-11β, 19-[4-(4-methoxyphenyl)-o-phenylene]-4,8-androstadien-3-one 17β-hydroxy-17α-(3-hydroxyprop-1(Z)-enyl)-11β, 19-[4-(4-methylthiophenyl)-o-phenylene]-4,8-androstadien-3-one 11β, 19-(4-acetyl-o-phenylene)-17β-hydroxy-17α-(3-hydroxyprop-1(Z)-enyl)-4,8-androstadien-3-one 11β, 19-(4-acetyl-o-phenylene)-17β-hydroxy-17α-(prop-1-inyl)-4,8-androstadien-3-one 17β-hydroxy-11β, 19-[4-(4-methylthiophenyl)-o-phenylene]-17α-(prop-1-inyl)-4,8-androstadien-3-one 17β-hydroxy-11β, 19-[4-(3-furanyl)-o-phenylene]-17α-(prop-1-inyl)-4,8-androstadien-3-one 17β-hydroxy-17α-(prop-1-inyl)-11β, 19-[4-(3-pyridyl)-ophenylene]-4,8-androstadien-3-one 17β-hydroxy-17α-methyl-11β, 19-[4-(4-cyanophenyl)-ophenylene]-4,8-androstadien-3-one 17α-cyanomethyl-17β-hydroxy-11β, 19-[4-(4-cyanophenyl)-ophenylene]-4,8-androstadien-3-one 17α-cyanomethyl-17β-hydroxy-11β, 19-[4-(4-dimethylaminophenyl)-o-phenylene]-4,8-androstadien-3-one 17β-hydroxy-17α-(3-hydroxyprop-1(Z)-enyl)-11β, 19-(4-vinylphenyl-o-phenylene)-4,8-androstadien-3-one 17β-hydroxy-11β, 19-(4-methylthiophenyl-o-phenylene)-17α-(prop-1-inyl)-4,8-androstadien-3-one 17β-hydroxy-17α-(3-hydroxyprop-1(Z)-enyl)-11β, 19-(4-methylsulfinylphenyl-o-phenylene)-4,8-androstadien-3-one 17β-hydroxy-17α-(3-hydroxyprop-1(Z)-enyl)-11β, 19-(4-methylthio-o-phenylene)-4,8-androstadien-3-one 17β-hydroxy-17α-(3-hydroxyprop-1(Z)-enyl)-11β, 19-(4-methylsulfinyl-o-phenylene)-4,8-androstadien-3-one 11β, 19-(4-dimethylamino-o-phenylene)-17β-hydroxy-17α-(3-hydroxyprop-1(Z)-enyl)-4,8-androstadien-3-one 11β, 19-[4-(4-dimethylaminophenyl)-o-phenylene]-17β-hydroxy-17α-(3-hydroxyprop-1(Z)-enyl)-4,8-androstadien-3-one 11β, 19-[4-(3-furyl)-o-phenylene]-17β-hydroxy-17α-(3-hydroxyprop-1(Z)-enyl)-4,8-androstadien-3-one 11β, 19-[4-(4-cyanophenyl)-o-phenylene]spiro[androsta-4,8-diene-17β, 2'(5'H)-furan]-3-one 11β, 19-[4-(4-cyanophenyl)-o-phenylene]-4',5'-dihydrospiro[androsta-4,8-diene-17β, 2'(3'H)-furan]-3-one 11β, 19-[4-(4-acetylphenyl)-o-phenylene]-17β-hydroxy-17α-(3-hydroxyprop-1-inyl)-4,8-androstadien-3-one 11β, 19-[4-(4-acetylphenyl)-o-phenylene]-17β-hydroxy-17α-(3-hydroxyprop-1(Z)-enyl)-4,8-androstadien-3-one 11β, 19-[4-(4-acetylphenyl)-o-phenylene]spiro[androsta-4,8-diene-17β, 2'(5'H)-furan]-3-one 11β, 19-[4-(4-acetylphenyl)-o-phenylene]-4',5'-dihydrospiro[androsta-4,8-diene-17β, 2'(3'H)-furan]-3-one 11β, 19-[4-(4-methylthiophenyl)-o-phenylene]spiro[androsta-4,8-diene-17β, 2'(5'H)-furan]-3-one 11β, 19-[4-(4-methylthiophenyl)-o-phenylene]-4', 5'-dihydrospiro[androsta-4,8-diene-17β, 2'(3'H)-furan]-3-one 11β, 19-(4-acetyl-o-phenylene)spiro[androsta-4,8-diene-17β, 2'(5'H)-furan]-3-one 11β, 19-(4-acetyl-o-phenylene)-4', 5'-dihydrospiro[androsta-4,8-diene-17β, 2'(3'H)-furan]-3-one.

According to the invention the new compounds of general formula I are produced by the process wherein a compound of general formula II.

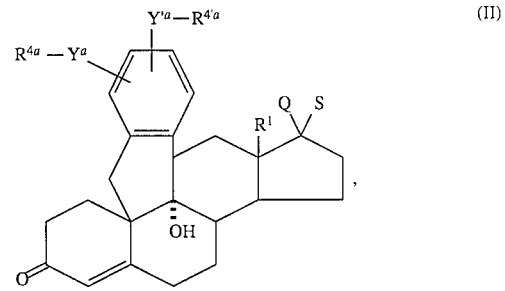

in which $R^{4a}$, $R^{4'a}$, $Y^a$ and $Y'^a$ have the same meaning as $R^4$, $R^{4'}$, $R^{4'}$, Y and Y' and optionally present hydroxy, mercapto, amino, oxo and/or terminal acetylene groups are protected, or $R^{4a}$–$Y^a$— and/or $R^{4'a}$–$Y'^a$— each mean a methoxy, hydroxy or perfluoroalkylsulfonate group, Q and S together mean an oxygen atom or one of the substituent combinations mentioned under $R^5/R^6$ that survives the subsequent reaction step of dehydration undamaged or in which free hydroxy groups are protected, by reaction with a dehydrating agent is converted in the corresponding 8-En-compound of general formula III

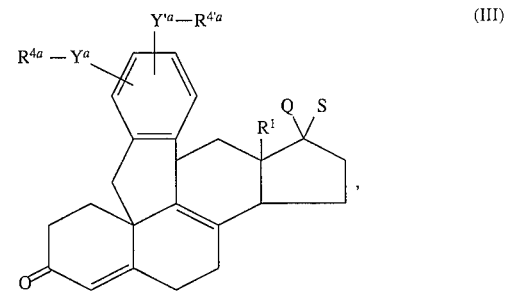

and then optionally if Q and S together mean an oxygen atom, the 3-keto function is selectively protected in the form of a corresponding dienolether, ketal or dithioketal and substituents $R^5/R^6$ or their precursors are introduced by nucleophile addition to the 17-keto function in a way known in the art (side chain synthesis), the 3-keto group is again released, then optionally, if $R^6$ is to mean $—(CH_2)_m—CH_2—R^9$ or $—CH=CH—(CH_2)_kCH_2—R^9$ the corresponding alkinyl compound is catalytically hydrogenated and optionally if $R^{4a}-Y^a—$ and/or $R^{4'a}-Y^{'a}—$ means a perfluoroalkyl-sulfonate group, that is generated ahead of time from a methoxy group by a hydroxy group, the perfluoroalkylsulfonate compound is converted into a compound either directly or by exchange of the perfluoroalkylsulfonate leaving group for a tin trialkyl group by the corresponding tin trialkyl compound, that in the 19, 11β-phenyl ring, optionally after additional reactions, has the desired substitution pattern, and this last mentioned process step of the aryl coupling can basically be performed at any step of the process according to the invention, the product thus obtained is optionally freed from protective groups, optionally the hydroxy, mercapto and/or amino group(s) contained in the 19, 11β-phenylene ring is/are alkylated or acylated, optionally the amino and/or sulfide group(s) optionally contained in the aryl substituent(s) is/are oxidized, optionally is reacted with hydroxylamine-hydrochloride to the product of general formula I with X meaning the hydroxyimino grouping >N-OH and optionally a pharmaceutically compatible acid addition salt is produced.

Preferably, thionyl chloride is used as dehydrating agent for cleaving of the 9α-hydroxy group.

The above-mentioned hydroxy, mercapto and keto protective groups are groups easily cleavable in acid medium such as, for example, methoxymethyl, ethoxymethyl, tetrahydropyranyl, ethylenedioxy ketal, ethylenedithio ketal or 2,2-dimethyltrimethylenedioxy ketal groups. One (or more) hydroxy group(s) present in the 19-phenyl ring is (are) protected by a group that can be removed by a base, for example by a methoxy group. The latter can be cleaved again for example by reaction with sodium thiophenolate.

Protective groups for amino and terminal acetylene groups (for example, the tri-methylsilyl group and the tert.-butyldimethylsilyl group) are also known to one skilled in the art and also cleaved in the desired reaction sequence according to processes known in the literature (Synthesis 1980, 627, J. Org. Chem. 46, (1986) 2280).

The 17-side chain synthesis for the end products of general formula I desired in the end takes place analogously to processes known in the literature (for example J. Fried, J. A. Edwards, "Organic Reactions in Steroid Chemistry," Van Nostrand Reinhold Company 1972, Vol 1 and 2; "Terpenoids and Steroids," Specialist Periodical Report, The Chemical Society, London, Vol. 1–12).

The oxidation of the 17β-hydroxy group necessary for the production of almost all end products is performed in a way known in the art, for example by Oppenauer oxidation or with chromic acid reagents (Jones reagent or chromic acid pyridine).

The release of the 3 keto function with simultaneous dehydration and formation of the 4(5)-double bond takes place by treatment with acid or an acid ion exchanger. The acid treatment takes place in a way known in the art, in which the corresponding 5α-hydroxy-3-ketal is dissolved in a water miscible solvent, such as aqueous methanol, ethanol or acetone, and catalytic amounts of mineral or sulfonic acid, such as hydrochloric acid, sulfuric acid, phosphoric acid, perchloric acid or p-toluene sulfonic acid, or an organic acid, such as acetic acid, is allowed to act on the solution until existing protective groups are removed and optionally the water is separated. The reaction that proceeds at temperatures of 0° to 100° C. can also be performed with an acid ion exchanger. The course of the reaction can be tracked with analytical methods, for example by thin-layer chromatography of samples taken.

A very special advantage of this invention lies in the large band width of the substituents which can be introduced in 19, 11β-phenylene radical (M. Pereyre, J.-P. Quintard, A. Rahm, Tin in Organic Synthesis; Butterworths, 1987). On the one hand the substituents $R^4-Y$ or $R^{4'}-Y'$ present in the later end product can be directly introduced, (compare EP-A 0283 428).

With another embodiment of the process according to the invention it is possible to vary the substituent(s) in the 19, 11β-phenylene radical by a wide range in which the substituent(s) is/are introduced first immediately before or even first after the formation of the 8,9-double bond. For this purpose at least one hydroxy group present and protected in the 19, 11β-phenylene radical of the initial product is released by its protective group and the corresponding perfluoroalkylsulfonate compound is produced from the free OH compound by reaction with perfluoroalkylsulfonic acid anhydride (alkyl=$C_1$–$C_4$) according to methods known in the art [P. J. Stang, M. Hanack and L. R. Subramanian, Synthesis 85 (1982)].

Here the course of action is either that the perfluorosulfonate leaving group is displaced by essentially almost simultaneous substitution by the desired substituent or its precursor in a transition metal catalyzed reaction (preferably Pd° ) (J. E. McMurry and S. Mohanraj, Tetrahedron Letters, 24, No. 27, pp 2723–2726, 1983; X. Lu and J. Zhu, Communications, pp 726–727, 1987; Q.-Y. Chen and Z.-Y. Yang, Tetrahedron Letters 27, No. 10, pp 1171–1174, 1986; S. Cacchi, P. G. Ciattini, E. Morera and G. Ortar, Tetrahedron Letters, 27, No. 33, pp 3931–3934, 1986; A. M. Echavarren and J. K. Stille, J. Am. Chem. Soc. 1987, 109, pp 5478–5486) or a corresponding triorganylstannyl compound, preferably tri-n-alkylstannyl compound is produced intermediately from the perfluoroalkylsulfonate compound and transition-metal catalyzed [J. K. Stille, Angew. Chem. 98 (1986), pp 504–519]. The triorganylstannyl compound, preferably the tri-n-alkylstannyl compound, is then reacted with a halogen, preferably bromine or iodine substituted carbocyclic (compare instructions 6c) under initial compounds) or heterocyclic atomatic substances (compare instructions 3b) initial compounds) [Y. Yamamoto, Y. Azuma, H. Mitoh, Communications, pp 564–565, 1986; T. J. Bailey, Tetrahedron Letters, 27, No. 37, pp 4407–4410, 1986], that optionally can have also other substituents; the 19, 11β-phenylene radical then has in it the desired precursor or a precursor of the desired substitution. The precursors are further processed according to common methods of organic chemistry to the finally desired compounds.

A relevant survey on aryl coupling reactions is found in J. Organometallic Chem. 392 (1990), p 285.

If the 19-phenyl ring has two protected hydroxy groups, then first only the protective group of one (first) hydroxy group is selectively removed, the free hydroxy group can be functionalized, then optionally the protective group of the second hydroxy group is cleaved off and this hydroxy group can be modified, optionally also by reaction with the function found now in the first hydroxy group.

The removal of the 3-oxo group to an end product of general formula I with X meaning two hydrogen atoms, e.g., can take place according to the instructions indicated in DE-A 2805490 by thioketalization and then reductive cleavage.

Feedstocks with a D-homo-steroid skeleton can also be obtained, e.g., by Tiffeneau rearrangement analogously to the instructions published in Australian J. Chem. 8 (1955), 519 and in "Organic Reactions in Steroid Chemistry" Vol 2, 388. The necessary 17α-aminomethyl-17β-hydroxy compounds are available for example by the opening of 17,20-spiroepoxides with ammonia or also by lithium aluminum reduction of the acetylated 17β-hydroxy-17α-cyano compounds. The spiro epoxides are available by reaction of the corresponding 17-ketones with dimethylsulfoniummethylide in dimethylformamide [Journal f. prakt. Chemie 314 (1972), 667–668]. The acetylated cyanohydrins are available by addition of hydrogen cyanide to the corresponding 17-ketones and then acetylation according to known instructions (e.g., Australian J. Chem. 8 (1955), 519).

Feedstocks with an unsaturated D ring are available for example by modified Saegusa oxidation (Tetrahedron 42 (1986) 2971) of the corresponding enol compounds of the 17 ketone. For example, the trimethylsilylenol ether is producible by converting the 17 ketone with lithium diisopropylamide in tetrahydrofuran into the corresponding enolate and trapping by trimethylchlorosilane (Synthesis 1983, 1).

The introduction of substituent $R^5$ and $R^6$ takes place according to usual processes of C-17-side chain synthesis by nucleophilic addition to the 17-ketone - obtained, e.g., by Oppenauer oxidation of the C-17-hydroxy groups—and subsequent reactions ("Terpenoids and Steroids," Specialist Periodical Report, The Chemical Society, London, Vol. 1–12).

The introduction of substituent —C≡_C–U as $R^6$, as $R^6$, and U has the above-mentioned meaning, takes place with the help of a compound of general formula MC≡_C–U', in which U is an alkine protective group, such as, for example, the trimethylsilyl or tert.-butyldimethylsilyl radical, or if U is an alkyl group with 1–4 C atoms, U' itself is the radical U.

The organometallic compound can also be formed in situ and brought into reaction with the 17-ketone. Thus, for example, acetylene and an alkali metal, especially potassium, sodium or lithium, in the presence of an alcohol or in the presence of ammonia can be allowed to act on the 17-ketone in a suitable solvent. The alkali metal can also take effect in the form of, for example, methyl or butyl lithium. Dialkylether, tetrahydrofuran, dioxane, benzene and toluene are especially suitable as solvents.

The introduction of 3-hydroxypropine, 3-hydroxypropene or 3-hydroxypropane in 17 position takes place by reaction of the 17-ketone with the dianion of propargyl alcohol (3-hydroxypropine), for example the dipotassium salt of propargyl alcohol generated in situ, to 17α-(3-hydroxyprop-1-inyl)-17β-hydroxy derivative or with metallized derivatives of 3-hydroxypropine, for example with 1-lithium-3-(tetrahydropyran-2'-yloxy)-prop-1-in-1-ide, to 17-[3-(tetrahydropyran-2'-yloxy)-prop-1-inyl]-17β-hydroxy derivative, that can then be hydrogenated to the 17-(3-hydroxypropyl- or hydroxypropenyl)-17β-hydroxy compounds. The latter is possible, for example, by hydrogenation at room temperature and normal pressure in solvents such as methanol, ethanol, propanol, tetrahydrofuran (THF) or ethyl acetate with addition of noble metal catalysts such as platinum or palladium.

The introduction of homologous hydoxyalkine, hydroxyalkene and hydroxyalkane groups takes place in a corresponding way with homologues of propargyl alcohol.

The compound with the Z configured double bond in the hydroxypropenyl group results by hydrogenation of acetylenic triple bond with a deactivated noble metal catalyst (J. Fried, J. A. Edwards: Organic Reactions in Steroid Chemistry, Van Nostrand Reinhold Company 1972, page 134; and H. O. House: Modern Synthetic Reactions 1972, page 19).

As deactivated noble metal catalysts, for example, 10% palladium on barium sulfate in the presence of an amine or 5% on palladium on calcium carbonate by addition of lead(II)acetate are suitable. The hydrogenation is ended after absorbing an equivalent of hydrogen.

The compound with the E configured double bond in the hydroxypropenyl group results by reduction of the acetylenic triple bond in a way known in the art. In the literature a whole series of methods for the conversion of alkines into transolefines are described, for example the reduction with sodium in liquid ammonia (J. Am. Chem. Soc. 63 (1941) 216), with sodium amide in liquid ammonia (J. Am. Chem. Soc. 1955, 3558), with lithium in low molecular amines (J. Am. Chem. Soc. 77 (1955) 3378), with boranes (J. Am. Chem. Soc. 93 (1971) 3395 and 94 (1972) 6560), with diisobutyl aluminum hydride and methyl-lithium (J. Am. Chem. Soc. 89 (1967) 5085) and especially with lithium aluminum hydride/alkoxide (J. Am. Chem. Soc. 89 (1967) 4245). Another possibility is the reduction of the triple bond with chromium(II)-sulfate in the presence of water or dimethylformamide in a weak acid medium (J. Am. Chem. Soc. 86 (1964) 4358) as well as generally the reduction by action of transition metal compounds with changing the oxidation steps.

The introduction of the hydroxyalkenes can also take place directly by addition of a corresponding metallized hydroxyalkenyl compound, such as, for example, 1-lithium-3-(tetrahydropyran-2'-yloxy)-prop-1(E)-ene (J. Org. Chem. 40 2265) or 1-lithium-3-(tetrahydropyran-2'-yloxy)-prop-1(Z)-ene (Synthesis 1981, 999). Homologues can also be introduced in this way.

The introduction of 3-hydroxypropane in 17 position can also take place directly by reaction of the 17 ketone with metallized derivatives of 3-halogen-propanols—and the hydroxy group is present in the metallization step as alcoholate (Tetrahedron Letters 1978, 3013) or as protected function (J. Org. Chem. 37, 1947)—to the 17-(3-hydroxypropyl)-17β-hydroxy compound or to the compound protected on the terminal hydroxy group. As protective group, for example, ethoxyethyl, tetrahydropyranyl and methoxymethyl groups are suitable.

If the end products of formula I are desired with $R^5/R^6$ meaning

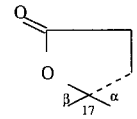

then the 17-(3-hydroxypropyl)-compound is oxidized in a way known in the art, for example, with Jones reagent, manganese dioxide, pyridinium dichromate, pyridinium chlorochromate, chromic acid-pyridine or the Fetizon reagent silver carbonate/Celite (Compt. rend. 267 [1968] 900).

The production of the end products of formula I with $R^5/R^6$ meaning

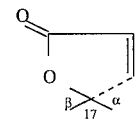

takes place by ring closure reaction of the corresponding 17-(3-hydroxyprop-1-(Z)enyl-17-β-hydroxy-feedstock.

If $R^5/R^6$ together are to stand for

then either a dihydrofuran compound described above is catalytically hydrogenated or the corresponding 17-(3-hydroxypropyl)-17β-hydroxy compound is cyclized.

The synthesis of the 17-cyanomethyl side chain takes place in a way known in the art from the 17-ketone, for example by the 17-spiro epoxide and cleavage of the spiro epoxide with HCN according to Z. Chem. 18 (1978) 259–260.

Also the introduction of the 17-hydroxyacetyl side chain takes place according to methods known in the art, for example according to methods described in J. Org. Chem. 47 (1982), 2993–2995, Chem. Ber. 113 (1984), 1184 or U.S. Pat. No. 4,600,538.

For the introduction of groupings

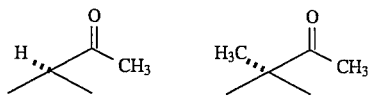

the 17-ketone is converted with tosylmethylisocyanide (Chem. Ind. 1972 213) into the 17-nitrile compound (Tetrahedron 31 (1975), 2151) that can be directly converted with methyl lithium or methyl magnesium bromide into the 17-acetyl compound, which yields the desired 17β-methyl-17β-acyl grouping after enolization with K-tert.-butylate in tetrahydrofuran and reaction with methyl iodide. This sequence of methyl addition to the nitrile and then alkylation can also be made in reverse sequence.

Free hydroxy or hydroxy, mercapto and/or amino groups present in Z or in the 19,11β-phenyl ring can be alkylated or acylated in a way known in the art.

Sulfides and/or dialkylamines contained in the 19,11β-phenylene ring can be converted by suitable oxidation agents (for example hydrogen peroxide or peracids) into the desired sulfoxides (n=1), N oxides (n=1) [see e.g., Kontakte (Darmstadt) 1986, 3, p. 12]or sulfones (n=2).

Compounds with a dialkyamine substituent in the 19, 11β-phenylene ring can be converted by reaction with bromocyanogen in aprotic solvents such as, for example, dioxane, benzene or toluene at a higher temperature (amine-degradation according to Braun) analogous to the instructions indicated, for example, in Org. Reactions 7, 198 (1953), K. W. Bentley, Techniques of Organic Chemistry 11, 773 (1963) and Houben-Weyl, 5/4, 151 (1960) in good yield into the corresponding (N-cyano-N-alkylaminoaryl) derivatives.

The latter, depending on the finally desired meaning of $R^{12}$ in the end product, are reduced in a way known in the art to the corresponding dialkyamine compounds (for.example with diisobutyl aluminum hydride into toluene to the N-formyl-N-alkyl aminophenyl intermediate products and then with lithium aluminum hydride) or N—H—N-alkyl compounds (for example with lithium aluminum hydride or with lithium in liquid ammonia). Then the latter are optionally acylated in a way known in the literature and then optionally reduced in a known way with, for example, lithium aluminum hydride to the new dialkylamine derivative (see DE 36 23 038).

The obtained compounds of general formula I with X meaning an oxygen atom optionally can be converted by reaction with hydroxylamine hydrochloride in the presence of tertiary amines at temperatures between −20° and +40° C. into the oximes (formula I with X meaning hydroxyimino grouping >N~OH, and the hydroxy group can be in syn or anti position. Suitable tertiary bases are, for example, trimethylamine, triethylamine, pryidine, N,N-dimethylaminopyridine, 1,5-diazabicyclo[4.3.0]nonene5 (DBN) and 1,5-diazabicyclo[5.4.0]undecene-5 (DBU), and pyridine is preferred.

The new compounds of general formula I as well as their pharmaceutically compatible addition salts with acids are valuable pharmaceutical agents. Thus they have a strong affinity for the progestogenic receptor and have a surprisingly large range of gestagen, antigestagen, antiglucocorticoid, antimineralcorticoid and antiandrogenic properties. These important biological actions can be used for medicinal purposes.

The strong affinity for the progestogenic receptor follows from the known progestogenic receptor binding test described i.a. in EP-A 0190 759. Accordingly the compounds according to the invention 11β, 19-[4-(4-cyanophenyl)-o-phenylene]-17β-hydroxy-17α-(3-hydroxyprop-1(Z)enyl)-4,8-androstadien-3-one (A) as well as 11β, 19-[4-(4-cyanophenyl)-o-phenylene]-17α-ethinyl-17β-hydroxy-4,8-androstadien-3-one (B) have K values of 1 or 0.7, which are evidence for a strong binding to the progestogenic receptor.

In comparison with the compounds described in EP-A 0 283 428, that have no 8,9-double bond, the compounds at hand are distinguished by a stronger bond to the gestagen receptor: the corresponding compounds analogous to compounds A & B, without 8,9-double bond only have K values of 7.5 and 5.6, respectively.

To show the antigestagen effect, the abortive effect on pregnant rats was determined according to the test described in EP-A 0 283 428. Accordingly compound A even at a dosage of 0.1 mg s.c. is completely abortively effective and compound B at a dosage of 0.3 mg s.c. is 75% abortively effective.

Active ingredients of this type with pronounced antigestagen activity are suitable for inducing abortions since they drive the progesterone necessary for maintaining pregnancy away from the receptor. Therefore they are of value and interest with respect to their use as birth control for women.

They can also be used to combat hormonal irregularities, for inducing menstruation and for inducing of labor.

Further they can be used for the treatment of hormone-dependent carcinomas.

The compounds of general formula I according to the invention as well as their pharmaceutically compatible addition salts with acids also have an antiglucocorticoid activity and thus can also be used as pharmaceutical agents for the treatment of corticoid-induced disorders (glaucoma) as well as for a means for combating the side effects that occur in long-term treatment with glucocorticoids (Cushing's syndrome). Therefore, they also make it possible to combat the disorders attributable to a supersecretion of glucocorticoids, above all obesity, arteriosclerosis, hypertension, osteoporosis, diabetes as well as insomnia.

The compounds according to the invention of general formula I as well as their pharmaceutically compatible addition salts with acids with gestagen activity can be used, for example, in the treatment of amenorrhea, dysmenorrhea, hypermenorrhea and luteal insufficiency, those with antimineral corticoid properties for the treatment of states of disease, in which a hyperaldosteronism is involved.

Thus the invention also relates to a pharmaceutical agents based on the pharmaceutical compatible compounds, i.e., in the used doses nontoxic compounds of general formula I as well as their pharmaceutically compatible addition salts with acids, optionally together with the usual auxiliary agents and vehicles.

The compounds according to the invention and their salts can be processed according to methods known in the art of galenicals for pharmaceutical preparations for enteral, percutaneous or local administration. They can be administered in the form of tablets, coated tablets, gel capsules, granular powders, suppositories, implants, injectable sterile aqueous or oily solutions, suspensions or emulsions, ointments, creams and gels.

In this way the active ingredient(s) can be mixed with the auxiliary agents usual in galenicals, such as, for example, gum arabic, talc, starch, mannitol, methyl cellulose, lactose, surfactants such as Tweens [R] or Myrj [R], magnesium stearate, aqueous or nonaqueous vehicles, paraffin derivatives, wetting agents, dispersing agents, emulsifiers, preservatives and aromatic substances for taste correction (e.g., essential oils).

Thus the invention also relates to pharmaceutical compositions that contain as active ingredient at least one compound according to the invention or one of its addition salts with pharmaceutically compatible acids.

As addition salts of the products with acids according to the invention especially hydrochlorides and methane sulfonates can be mentioned. A dosage unit contains approximately 1–100 mg of active ingredient(s).

The dosage of the compounds according to the invention in humans is at approximately 0.1–1000 mg per day, preferably 0.1–300 mg per day.

The following examples explain the production of the compounds according to the invention.

The production of the initial compounds necessary according to the invention takes place according to the following diagram:

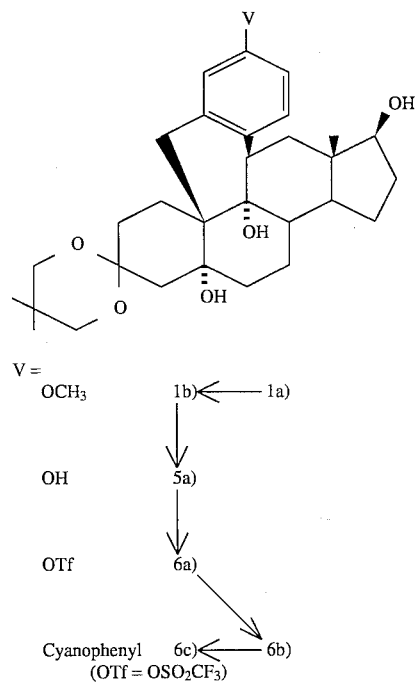

Cyanophenyl takes place from 6) oxidation analogous to 1c). Survey article for couplings: J. Organometallic Chem. 392 (1990) 285

The physical data of these initial compounds is found in table 1.

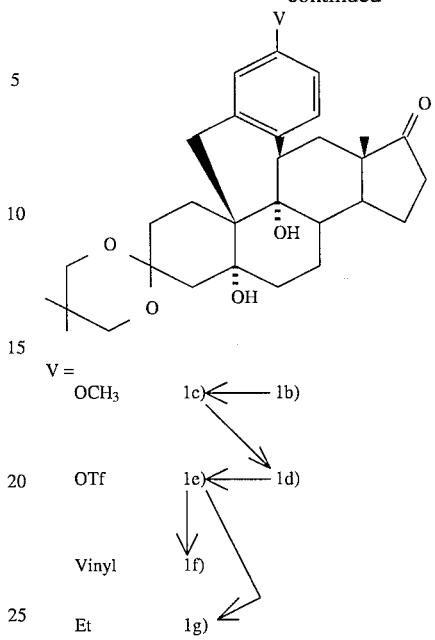

TABLE 1

| X = | Melting Point (crystallized out) | $[\alpha]_D^{20}$ (solvent; concentration) |
|---|---|---|
| $OCH_3$ | 254–255° C. (EE) | 31° ($CHCl_3$; 0.51) |
| OH | 242–244° C. (DIPE/$CH_2Cl_2$) | 32° ($CHCl_3$; 0.51) |
| OTf | 176–178° C. (DIPE/$CH_2Cl_2$) | 29° ($CHCl_3$; 0.51) |
| Cyanophenyl | 302–305° C. (EE) | 56° ($CHCl_3$; 0.51) |

TABLE 1-continued

| X = | Melting Point (crystallized out) | $[\alpha]_D^{20}$ (solvent; concentration) |
|---|---|---|
| OCH$_3$ | 270–271° C. (MeOH/EE) | 46° (CHCl$_3$; 0.5) |
| OTf | 205–208° C. (EE) | 40° (CHCl$_3$; 0.51) |
| Vinyl | 273–275° C. (DIPE/CH$_2$Cl$_2$) | |
| Et | 260–261° C. (EE) | 49° (CHCl$_3$; 0.51) |
| Cyanophenyl | 296–299° C. (EE) | 72° (CHCl$_3$; 0.515) |

EE = Ethylacetate; DIPE = Diisopropylether; MeOH = Methanol.

25.5 g (50 mml) of 5α, 9α-dihydroxy-3,3-(2,2-dimethyltrimethylenedioxy)-11β, 19-(4-methoxy-o-phenylene)-androstan-17-one is dissolved in 250 ml of absolute dimethylformamide and mixed under protective gas with 14 g of sodium thiomethylate. Under an inert gas atmosphere the reaction mixture is refluxed for 3 hours, then cooled to room temperature and then poured on 4 l of ice water. It is stirred until the crude product is flocculated as a white solid. Then it is suctioned off, washed with a lot of water and dried in a vacuum. 22.6 g of the title compound is obtained as crude product, whose purity is sufficient for the following reactions.

Instructions for the production of the initial compounds:

1) 9α, 17β-Dihydroxy-11β, 19-(4-ethyl-o-phenylene)-17-(prop-1-inyl)-4-androsten-3-one a) 19-(2-Bromo-5-methoxyphenyl)-3,3-(2,2-dimethyltrimethylenedioxy)-9α,11α-epoxy-androstane-5α, 17β-diol To a solution of 47.6 g (82.6 mmol), 19-(2-bromo-5-methoxyphenyl)-3,3-(2,2-dimethyltrimethy! enedioxy)-9,11-androstene-5α, 17β-diol (EP-A 0283428) in 0.8 of 1 of methylene chloride is added in succession at room temperature 225 ml of a 0.5 m aqueous sodium bicarbonate solution and 22.6 g of 67% mchloroperbenzoic acid. Then the reaction mixture is stirred for 1.5 hours more. For working up, the aqueous phase is separated, extracted with a little methylene chloride and the organic phases are combined. The latter are washed in succession with saturated sodium thiosulfate solution, 5% sodium hydroxide solution and water, dried on sodium sulfate and concentrated by evaporation in a vacuum. The purity of the crude product (47.4 g) is sufficient for the other reaction under b). For characterization, 400 mg of crude product is chromatographed on silica gel with a mixture of ethyl acetate/hexane. 357 mg of 19-(2-bromo-5-methoxyphenyl)-3,3-(2,2-dimethyltrimethylenedioxy)-9α, 11α-epoxy-androstane-5α, 17β-diol is obtained.

b) 3,3-(2,2-Dimethyltrimethylenedioxy)-11β, 19-(4-methoxy-o-phenylene)-androstane-5α,9α-17β-triol 41.4 g (70 mmol) of 19-(2-bromo-5-methoxyphenyl)-3,3-(2,2-dimethyltrimethylenedioxy)-9α,11α-epoxy-androstane-5α,17β-diol, dissolved in 350 ml of absolute diethyl ether, is added under protective gas at room temperature to 435 ml of a 0.8 ethereal methyl magnesium iodide solution. After.30 minutes more stirring the reaction mixture is mixed with 825 ml of a 1.6 m n-butyllithium solution (hexane) and stirred again overnight. Then it is carefully poured on ice cooled saturated aqueous ammonium chloride solution, the organic phase is separated and the aqueous phase extracted again with ethyl acetate. The organic phases are combined, washed with saturated, aqueous common salt solution, dried on sodium sulfate and concentrated by evaporation in a vacuum. The crude product (37.2 g) is chromatographed on silica gel with a mixture of ethyl acetate/hexane and 31.3 g of the title compound is obtained as white foam.

Melting point: =254-255° C (ethyl acetate).

c) 5α, 9α-Dihydroxy-3,3-(2,2-dimethyltrimethylenedioxy)-11β, 19-(4-methoxy-o-phenylene)-androstan-17-one 35.1 g of chromiumtrioxide is added in portions to a mixture of 120 ml of pyridine and 875 ml of methylene chloride at 0° C. Then 30 g of 3,3-(2,2-dimethyltrimethylenedioxy)-11β, 19-(4-methoxy-o-phenylene)-androstane-5α, 9α-17β-triol, dissolved in 100 ml of methylene chloride, is slowly instilled at the same temperature and the reaction mixture is stirred another 1.5 hours at ice bath temperature. After completion of the stirring the solid components are allowed to settle, the supernatant phase is decanted and the precipitate is thoroughly washed several times with methylene chloride. The combined organic phases are freed of residual inorganic components bywashing with 0.5 m potassium hydroxide solution, washed neutral with water, dried on sodium sulfate and conoentrated by evaporation in a vacuum. 26.7 g of the title compound is isolated as white foam by chromatography of the residue on silica gel with a mixture of ethyl acetate/hexane.

d) 5α,9α-Dihydroxy-3,3-(2,2-dimethyltrimethylenedioxy)-11β, 19-(4-hydroxy-o-phenylene)-androstan-17-one 25.5 g (50 ml) of 5α, 9α-dihydroxy-3,3-(2,2-dimethyltrimethylenedioxy)-11β, 19-(4-methoxy-o-phenylene)-adrostan-17-one is dissolved in 250 ml of absolute dimethylformamide and mixed under protective gas with 14 g of sodium thiomethylene. Under an inert gas atmosphere the reaction mixture is refluxed for 3 hours, then cooled to room temperature and then poured on 4 l of ice water. It is stirred under the crude product is fluocculated as a white solid. Then it is suctioned off, washed with a lot of water and dried in a vacuum. 22.6 g of the title compound is obtained as crude product, whose purity is sufficient for the following reactions.

e) 5α, 9α-Dihydroxy-3,3-(2,2-dimethyltrimethylenedioxy)-11β, 19-(4-trifluoromethane-sulfonyloxy-o-phenylene)-androstan-17-one 21.85 g (44 mmol) of 5α, 9α-dihydroxy-3,3-(2,2-dimethyltrimethylenedioxy)-11β, 19-(4-hydroxy-o-phenylene)-androstan-17-one is dissolved in 675 ml of absolute methylene chloride and mixed with 29.8 g of 4-dimethylaminopyridine. The solution is then cooled to −70° C. under protective gas and mixed by slow instillation with 9.7 ml of trifluoromethane sulfonic acid anhydride dissolved in 60 ml of absolute methylene chloride. After 30 minutes more of stirring at −70° C. the reaction mixture is poured on saturated aqueous sodium bicarbonate solution, the organic phase is separated and the aqueous phase extracted several times with methylene chloride. The combined organic phases are washed with saturated sodium chloride solution, dried on sodium sulfate and concentrated by evaporation in a vacuum. 23.1 g of the title compound is obtained as white foam after chromatography of the residue on silica gel with a mixture of ethyl acetate/hexane.

f) 5α, 9α-Dihydroxy-3,3-(2,2-dimethyltrimethylenedioxy)-11β, 19-(4-vinyl-o-phenylene)-androstan-17-one 4 g of 5α, 9α-dihydroxy-3,3-(2,2-dimethyltrimethylenedioxy)-11β, 19-(4-trifluoromethane-sulfonyloxy-o-phenylene)-androstan-17-one is dissolved in 64 ml of absolute dimethyl formamide and mixed with 542 mg of lithium chloride, 0.37 g of tetrakistriphenyl palladium and 2.34 ml of tributylvinyl tin. Then the reaction mixture is stirred for 1.5 hours at 110° C. under protective gas and then cooled to room temperature. After filtration on Celite and washing of the filter residue with ethyl acetate the organic phase is washed with saturated sodium chloride solution, dried on sodium sulfate and concentrated by evaporation in a vacuum. Chromatography of the residue on silica gel with a mixture of ethyl acetate/hexane yields 2.96 g of the title compound as white foam.

g) 5α, 9α-Dihydroxy-3,3-(2,2-dimethyltrimethylenedioxy)-11β, 19-(4-ethyl-o-phenylene)-androstan-17-one 1.5 g of 5α, 9α-dihydroxy-3,3-(2,2-dimethyltrimethylenedioxy)-11β, 19-(4-vinyl-o-phenylene)-androstan-17-one is dissolved in 15 ml of absolute tetrahydrofuran and after addition of 1.5 ml of pyridine with 150 mg of palladium is hydrogenated on barium sulfate (10%) as catalyst at normal presssure. After absorbing an equivalent hydrogen the reaction mixture is suctioned off on Celite, the filter residue is washed again with ethyl acetate and the filtrate concentrated by evaporation in a vacuum. Crystallization of the crude product from ethyl acetate leads to 1.26 g of the title compound.

h) 3,3-(2,2-Dimethyltrimethylenedioxy)-11β, 19-(4-ethyl-ophenylene)-17-(prop-1-inyl)-androstane-5α, 9α-17β-triol 30 ml of absolute tetrahydrofuran is saturated with propine at 0° C. Then 3.7 ml of a 1.6 m-butyllithium solution (hexane) is slowly instilled in this solution without a greater increase in temperature. After 15 minutes more of stirring a solution of 300 mg of 5α,9α-dihydroxy-3,3-(2,2-dimethyltrimethylenedioxy)-11β, 19-(4-ethyl-o-phenylene)-androstan-17-one, dissolved in 6 ml of absolute tetrahydrofuran, is slowly instilled in this reaction mixture with ice bath cooling and allowed to be stirred again overnight. Then the reaction mixture is poured on water, the aqueous phase extracted with ethyl acetate and the organic phase washed with sodium chloride solution. After drying on sodium sulfate and concentrating by evaporation of the organic phase in a vacuum the residue is chromatographed on aluminum oxide (neutral, step III). 295 mg of the title compound is obtained as white foam.

i) 9α, 17β-Dihydroxy-11β, 19-(4-ethyl-o-phenylene)-17-(prop-1-inyl)-4-androsten-3-one 280 mg of 3,3-(2,2-dimethyltrimethylenedioxy)-11β, 19-(4-ethyl-o-phenylene)-17-(prop-1-inyl)-androstane-5α, 9α-17β-triol is dissolved in 20 ml of acetone and mixed with 0.1 ml of 4 n aqueous hydrochloric acid. After 3 hours more of stirring at 40° C. the reaction mixture is poured on saturated sodium bicarbonate solution and the aqueous phase extracted with methylene chloride. The combined organic phases are washed with saturated sodium chloride solution, dried on sodium sulfate and concentrated by evaporation in a vacuum. 234 mg of the title compound is obtained as white foam after chromatography of the residue on silica gel with a mixture of ethyl acetate/hexane.

Melting point: =155°–160° C. (hexane/methylene chloride)

2) 9α,17β-Dihydroxy-11β, 19-(4-vinyl-o-phenylene)-17-(prop-1-inyl)-4-androsten-3-one a) 3,3-(2,2-Dimethyltrimethylenedioxy)-11β, 19-(4-vinyl-o-phenylene)-17-(prop-1-inyl)-androstane-5α, 9α-17β-triol Analogously to the instructions described in 1h) 1 g of the keto compound produced in f is converted into the corresponding 17-propinyl compound. 0.97 g of the above compound is obtained as white foam.

b) 9α, 17β-Dihydroxy-11β, 19-(4-vinyl-o-phenylene)-17-(prop-1-inyl)-4-androsten-3-one Analogously to the instructions described in 1i) 0.9 g of the propinyl compound produced in d) is reacted. 660 mg of the title compound is obtained as white foam.

Melting point: 171°–175° C. (diisopropylether/methylene chloride)

3) 9α, 17β-Dihydroxy-11β, 19-[4-(3-pyridyl)-o-phenylene]-17-(prop-1-inyl)-4-androsten-3-one a) 5α, 9α-Dihydroxy-3,3-(2,2-dimethyltrimethylenedioxy)-11β, 19-(4-tri-n-butylstannyl-o-phenylene)-androstan-17-one 2.6 g of the triflate produced in 1e) is dissolved in 41 ml of absolute dioxane and mixed under protective gas with 6.2 ml of hexa-n-butyl tin, 521 mg of lithium chloride and 190 mg of tetrakistriphenylphosphinepalladium. Then the reaction mixture is heated to 110° C. stirred for 1 hour more, cooled to room temperature and concentrated by evaporation in a vacuum. The residue is chromatographed on silica gel with a mixture of ethyl acetate/hexane. 2.75 g of the above compound is obtained as white foam.

b) 5α, 9α-Dihydroxy-3,3-(2,2-dimethyltrimethylenedioxy)-11β, 19-[4-(3-pyridyl)-o-phenylene]-androstan-17-one 2.7 g of the tin organyl produced in a) is dissolved in 41 ml of absolute toluene, mixed with 190 mg tetrakistriphenylphosphinepalladium and 4 ml of 3-bromopyridine. Then the reaction mixture is heated for 17 hours to 110° C., cooled to room temperature and concentrated by evaporation in a vacuum. The residue is chromatographed on silica gel with a mixture of ethyl acetate/hexane. 1.47 g of the above compound is obtained as white foam.

c) 3,3-(2,2-Dimethyltrimethylenedioxy)-11β, 19-[4-(3-pyridyl)-o-phenylene]-17-(prop-1-inyl)-androstane-5α, 9α-17β-triol Analogously to the instructions described in 1h) 400 g of the keto compound produced in b) is converted into the corresponding 17-propinyl compound. 402 mg of the above compound is obtained as white foam.

d) 9α, 17β-Dihydroxy-11β, 19-[4-(3-pyridyl)-o-phenylene]-17(prop-1-inyl)-4-androsten-3-one Analogously to the instructions described in 1i) 380 mg of the propinyl compound produced in c) is reacted. 288 mg of the title compound is obtained as white foam.

Melting point: 203°–205° C. (diisopropylether)

4) 9α, 17β-Dihydroxy-11β, 19-(4-methoxy-o-phenylene]-4-androsten-3-one

Analogously to the instructions described in 1i) 0.5 g of the hydroxy compound produced in 1b) is reacted. 306 mg of the title compound is obtained as white foam. Melting point: 175°–177° C. (ethyl acetate).

5) 9α, 17β-Dihydroxy-11β, 19-(4,hydroxy-o-phenylene)-4-androsten-3-one a) 3,3-(2,2-Dimethyltrimethylenedioxy)-11β, 19-(4-hydroxy-o-phenylene)-androstane-5α9α-17β-triol Analogously to the instructions described in 1d) 2.5 g of the methoxy compound produced in 1b) is reacted. After chromatography on silica gel with a mixture of ethyl acetate/hexane, 2.15 g of phenol is obtained as white foam.

b) 9α, 17β-Dihydroxy-11β, 19-(4-hydroxy-o-phenylene)-4-androsten-3-one

Analogously to the instructions described in li) 750 mg of phenol produced in a) is reacted. 394 mg of the title compound is obtained as white foam. Melting point: 146°–148° C. (ethyl acetate).

6) 9α,17β-Dihydroxy-11β, 19-[4-(4-cyanophenyl)-o-phenylene]-4-androsten-3-one a) 3,3-(2,2-Dimethyltrimethylenedioxy)-11β, 19-(4-trifluoromethanesulfonyloxy-o-phenylene)-androstane-5α, 9α-17β-triol Analogously to the instructions described in 1e) 1.25 g of the phenol produced in 5a) is reacted. After chromatography on silica gel with a mixture of ethyl acetate/hexane, 1.3 g of triflate is obtained as white foam.

b) 3,3-(2,2-Dimethyltrimethylenedioxy)-11β, 19-(4-tri-n-butylstannyl-o-phenylene)-androstane-5α, 9α-17β-triol Analogously to the instructions described in 3a) 1.25 g of the triflate produced in a) is reacted. After chromatography on silica gel with a mixture of ethyl acetate/hexane, 1.53 g of tin organyl is obtained as white foam.

c) 3,3-(2,2-Dimethyltrimethylenedioxy)-11β, 19-[4-(4-cyanophenyl)-o-phenylene]-androstane-5α, 9α-17β-triol Analogously to the instructions described in 3b) 1.5 g of the tin organyl produced in b) is reacted with 4 g of 4-bromobenzene nitrile. After chromatography on silica gel with a mixture of ethyl acetate/hexane, 0.73 g of coupling product is obtained as white foam.

d) 9α, 17β-Dihydroxy-11β, 19-[4-(4-cyanophenyl)-o-phenylene]-4-androsten-3-one

Analogously to the instructions described in 1i) 700 mg of benzene nitrile produced in c) is reacted. 512 mg of the title compound is obtained as white foam. Melting point: 186°–190° C. (diisopropylether).

EXAMPLE 1

17β-Hydroxy-11β, 19-(4-methoxy-o-phenylene)-17α-(prop-1-inyl)-4,8-androstadien-3-one a) 9α-Hydroxy-11β, 19-(4-methoxy-o-phenylene)-4-androstene-3,17-dione 2.75 g of 5α, 9α-dihydroxy-3,3-(2,2-dimethyltrimethylenedioxy)-11 β, 19-(4-methoxy-o-phenylene)-androstan-17-one is dissolved in 150 ml of acetone and mixed under protective gas with 7.5 ml of 4 n aqueous hydrochloric acid. After 3 more hours of stirring at 40° C. the reaction mixture is poured on cold saturated sodium bicarbonate solution and the aqueous phase is extracted several times with methylene chloride. The combined organic phases are dried on sodium sulfate and concentrated by evaporation in a vacuum. The residue is chromatographed on silica gel with a mixture of ethyl acetate/hexane. 1.96 g of 9α-hydroxy-11β, 19-(4-methoxy-o-phenylene)-4-androstene-3,17-dione is obtained as white foam.

Melting point: 114° C. (ethyl acetate)

b) 11β, 19-(4-Methoxy-o-phenylene)-4,8-androstadiene-3,17-dione 1.8 g of 9e-hydroxy-11β, 19-(4-methoxy-o-phenylene)-4-androstene-3,17-dione is dissolved in 21 ml of absolute pyridine and slowly mixed with 0.31 ml of thionyl chloride at 0° C. After 30 minutes more of stirring the reaction mixture is carefully stirred in saturated sodium bicarbonate solution and the aqueous phase is extracted several times with ethyl acetate. The combined organic phases are washed with saturated sodium chloride solution, dried on sodium sulfate and concentrated by evaporation in a vacuum. The residue is chromatographed on silica gel with a mixture of ethyl acetate/hexane. 1.26 g of 11β, 19-(4-methoxy-o-phenylene)-4,8-androstadiene-3,17-dione is obtained as white foam.

c) 3-Ethoxy-11β, 19-(4-methoxy-o-phenylene)-3,5,8-androstatrien-17-one 1 g of 11β, 19-(4-methoxy-o-phenylene)-4,8-androstadiene-3,17-dione is dissolved in 26 ml of absolute methylene chloride and mixed in succession with 2.6 ml of triethylorthoformate, 0.17 ml of absolute ethanol and 14 mg of para-toluene sulfonic acid at 0° C. After 4 more hours of stirring triethylamine (0.1 ml) is added to the reaction mixture, the reaction solution is then stirred in saturated sodium bicarbonate solution and the aqueous phase is extracted several times with methylene chloride. The combined organic phases are washed with saturated sodium chloride solution, dried on sodium sulfate and concentrated by evaporation in a vacuum. The residue is used directly in the following reaction step.

d) 3-Ethoxy-11β, 19-(4-methoxy-o-phenylene)-17α-(prop-1-inyl)-3,5,8-androstatrien-17β-ol 120 ml of absolute tetrahydrofuran is dissolved with propine at 0° C. Then 16 ml of a 1.6 m n-butyllithium solution (hexane) is slowly instilled in this solution without a sizable increase in temperature. After 15 minutes more of stirring a solution of the ketone produced in c), dissolved in 25 ml of absolute tetrahydrofuran, is slowly instilled at ice-bath cooling to this reaction mixture and it is allowed to stir for 60 minutes more. Then the reaction mixture is poured on water, the aqueous phase is extracted with ethyl acetate and the organic phase is washed with sodium chloride solution. After drying on sodium sulfate and concentration by evaporation in a vacuum of the organic phase, the residue, as described in the following instructions, is directly further reacted.

e) 17β-Hydroxy-11β, 19-(4-methoxy-o-phenylene)-17α-(prop-1-inyl)-4,8-androstadien-3-one The residue obtained in d) is reacted to the title compound analogously to the instructions described in a). After chromatography on silica gel with a mixture of ethyl acetate/hexane 332 mg of the title compound is isolated as yellowish foam.

Melting point: 250°–253° C. (ethyl acetate)

$[\alpha]^{20}_D = +70°$ (CHCl$_3$; c=0.525)

EXAMPLE 2

11β, 19-(4-Ethylphenyl-o-phenylene)-17β-hydroxy-17α-(prop-1-inyl)-4,8-androstadien-3-one A) In an analogous sequence of the reaction instructions described in example 1, 296 mg of the title compound is produced as yellowish foam starting from 2.2 g of 11β, 19-(4-ethyl-o-phenylene)-5α, 9α-dihydroxy-3,3-(2,2-dimethyltrimethylenedioxy)-androstan-17-one by a) 11β, 19- (4-ethyl-o-phenylene) -9α-hydroxy-4-androstene-3, 17-dione, b) 11β, 19- (4-ethyl-o-phenylene) -4,8-androstadiene-3,17-dione, c) 3-ethoxy-11β, 19- (4-ethyl-ophenylene)-3,5,8-androstatrien-17-one and d) 3-ethoxy-11β, 19-(4-ethyl-o-phenylene)-17α-(prop-1-inyl)-3,5,8-androstatrien-17β-ol.

$^1$H-NMR (CDCl$_3$) [δ] ppm: 7.27 (1H, d J=8.5 Hz); 7.05 (1H, dd J$_1$=8.5 and J$_2$=1.5 Hz); 6.84 (1H, d J=1.5 Hz); 5.89 (1H,s); 3.73 (1H, d broad J=7.5 Hz); 3.12 (1H, d J=17.5 Hz); 2.94(1H, d J=17.5 Hz); 1.22 (3H, tr 4 J=7.5 Hz); 0.54 (3H,s)

$[\alpha]^{20}_D = +74°$ (CHCl$_3$; c=0 465)

B) Alternatively 325 mg of the title compound can be produced starting from 1.3 g of 11β, 19-(4-ethyl-o-phenylene)-4,8-androstadiene-3,17-dione by selective ketalization to 11β, 19-(4-ethyl-o-phenylene)-3,3-(2,2-dimethyltrimethylenedioxy)-5,8-androstadien-17-one$^1$, propine addition to 11β, 19-(4-ethyl-o-phenylene)-3,3-(2,2-dimethyltrimethylenedioxy)-17α-(prop-1-inyl)-5,8-androstadien-17β-ol analogously to instructions 1 d) and acid cleavage analogous to instructions 1 a).

$^1$11β, 19-(4-Ethyl-o-phenylene)-3,3-(2,2-dimethyltrimethylenedioxy)-5,8-androstadien-17-one 1.3 g of 11β, 19-(4-ethyl-o-phenylene)-4,8-androstadiene-3,17-dione is dissolved in 85 ml of absolute methylene chloride and mixed in succession with 0.9 ml of trimethylorothoformate, 1.8 g of 2,2-dimethyl-1,3-propanediol and 50 mg of para-toluene sulfonic acid. After 4 more hours of stirring triethylamine (0.5 ml) is added to the reaction mixture, the reaction solution is then stirred in saturated sodium bicarbonate solution and the aqueous phase is extracted several times with methylene chloride. The combined organic phases are washed with saturated sodium chloride solution, dried on sodium sulfate and concentrated by evaporation in a vacuum. The residue is chromatographed on silica gel with a mixture of ethyl acetate/hexane. 778 mg of 11β, 19-(4-ethyl-o-phenylene)-3,3-(2,2-dimethyltrimethylenedioxy)-5,8-androstadien-17-one is obtained as white foam.

Melting point: 145°–147° C. (diisopropylether)

EXAMPLE 3

11β, 19-[4-(4-Cyanophenyl)-o-phenylene]-17β-hydroxy-17α-(prop-1-inyl)-4,8-androstadien-3-one In an analogous sequence of the reaction instructions described in example 1, 312 mg of the title compound is produced as yellowish foam starting from 2.7 g of 11β, 19-[4-(4-cyanophenyl)-o-phenylene]-5α, 9α-dihydroxy-3,3-(2,2-dimethyltrimethylenedioxy)-androstan-17-one by a) 11β, 19-[4-(4-cyanophenyl)-o-phenylene]-9α-hydroxy-androstene-3,17-dione, b) 11β, 19-[4-(4-cyanophenyl)-o-phenylene]-4,8-androstadien-3,17-dione, c) 11β, 19-[4-(4-cyanophenyl)-o-phenylene]-3-ethoxy-3,5,8-androstatrien-17-one and d) 11β, 19-[4-(4-cyanophenyl)-ophenylene]-3-ethoxy-17α-(prop-1-inyl)-3,5,8-androstatrien-17β-ol.

Melting point: 209°–211° C. (methylene chloride/diisopropylether)

$[\alpha]_{20D} = +94°$ (CHCl$_3$; c=0.505)

EXAMPLE 4

11β, 19-[4-(4-Cyanophenyl)-o-phenylene]-17α-ethinyl-17β-hydroxy-4,8-androstadien-3-one In an analogous sequence of the reaction instructions described in example 1, 341 mg of the title compound is produced as yellowish foam starting from 2.7 g of 11β, 19-[4-(4-cyanophenyl)-o-phenylene]-5α, 9α-dihydroxy-3, 3-(2,2-dimethyltrimethylenedioxy)-androstan-17-one by a) 11β, 19-[4-(4-cyanophenyl)-o-phenylene]-9α-hydroxy-4-androstene-3,17-dione, b) 11β, 19-[4-(4-cyanophenyl)-o-phenylene]-4,8-androstadiene-3,17-dione, c) 11β, 19-[4-(4-cyanophenyl)-o-phenylene]-3-ethoxy-3,5,8-androstatrien-17-one and d) 11β, 19-[4-(4-cyanophenyl)-ophenylene]-17α-ethinyl-3-ethoxy-3,5,8-androstatrien-17β-ol.

Melting point: 212°

14 215° C. (ethyl acetate)

$[\alpha]^{20}_D = +155°$ (CDCl$_3$; c=0.515)

EXAMPLE 5

11β, 19-[4-(4-Cyanophenyl)-o-phenylene]-17β-hydroxy-17α-(3-hydroxyprop-1-inyl)-4,8-androstadien-3-one A) In an analogous sequence of the reaction instructions described in example 1, 854 mg of the title compound is produced as yellowish foam starting from 5.7 g of 11β, 19-[4-(4-cyanophenyl)-o-phenylene]-5α,9α-dihydroxy-3,3-(2,2-dimethyltrimethylenedioxy)-androstan-17-one by a) 11β, 19-[4-(4-cyanophenyl)-o-phenylene]-9α-hydroxy-4-androstene-3,17-dione, b) 11β, 19-[4-(4-cyanophenyl)-o-phenylene]-4,8-androstadiene-3,17-dione, c) 11β, 19-[4-(4-cyanophenyl)-o-phenylene]-3-ethoxy-3,5,8-androstatrien-17-one and d) 11β, 19-[4-(4-cyanophenyl)-o-phenylene]-3-ethoxy-17α-[3-(tetrahydropyran-2-yloxy)-prop-1-inyl ]-3,5,8-androstatrien-17β-ol[2].

$^1$H-NMR (CDCl$_3$) [δ]ppm: 7.65–7.77 (4H, m); 7.4–7.53 (2H, m); 7.26 (1H, s); 5.93 (1H, s); 4.35 (2H, d J=5 Hz); 3.81 (1H, d broad J=7.5 Hz); 3.22 (1H, d J=17.5 Hz); 3.05 (1H, d J=17.5 Hz); 0.58 (3H, s)

[2]The addition of 3-(tetrahydropyran-2-yloxy)-prop-1-ine takes place analogous to instructions 1 d). The procedure is performed with a 19-fold excess of the corresponding lithium actylide.

B) Alternatively the title compound can also be obtained by
a) production of 17β-hydroxy-17α- (3-hydroxyprop-1-inyl) -11β, 19-[4-tri-n-butyl tannyl-o-phenylene]-4,8-androstadien-3-one[3] and b) coupling with 4-bromobenzonitrile analogously to the instructions described in examples 7 a) and b) . 1.14 g of the title compound is obtained starting from 2 g of the triflate produced in example 8a).

[3] $^1$H-NMR (CDCl$_3$) [δ]ppm: 7.28 (2H, s) ; 7.07 (1H, s) ; 5.9 (1H, s); 4.38 (2H d J=6 Hz); 3.74 (1H, m); 3.12 (1H, d J=17.5 Hz); 2.96 (1H, d J=17.5 Hz); 0.87 (9H, tr J=7.5 Hz); 0.54 (3H, s)

EXAMPLE 6

11β, 19-[4-(4-Cyanophenyl)-o-phenylene]-17β-hydroxy-17α-(3-hydroxyprop-1(Z)-enyl)-4,8-androstadien-3-one 500 mg of 11β, 19-[4-(4-cyanophenyl)-o-phenylene]-17β-hydroxy-17α-(3-hydroxyprop-1-inyl)-4,8-androstadien-3-one is dissolved in 20 ml of tetrahydrofuran, mixed with 0.5 ml of pyridine and hydrogenated using 50 mg of palladium (10%) on barium sulfate as catalyst at normal pressure. After absorbing an equivalent of hydrogen the reaction mixture is filtered on Celite, the filter residue is washed again with ethyl acetate and methylene chloride and the filtrate concentrated by evaporation in a vacuum. The residue is chromatographed on silica gel with a mixture of ethyl acetate/hexane. 412 mg of the title compound is obtained.

Melting point: 214°–216° C. (ethyl acetate)
$[α]^{20}_D$=+213° (CHCl$_3$; c=0.52)

EXAMPLE 7

17β-Hydroxy-17α-(prop-1-inyl)-11β, 19-[4-(5-pyrimidinyl)-o-phenylene]-4,8-androstadien-3-one a) 17β-Hydroxy-17α-(prop-1-inyl)-11β, 19-(4-trifluoromethylsulfonyloxy-o-phenylene)-4,8-androstadien-3-one In an analogous sequence to the reaction instructions described in example 1, 3.7 g of 17β-hydroxy-17α-(prop-1-inyl)-11β, 19-(4-trifluoromethylsulfonyloxy-o-phenylene)-4,8-androstadien-3-one is produced as yellowish foam starting from 15 g of 11β, 19-(4-trifluoromethylsulfonyloxy-o-phenylene)-5α,9α-dihydroxy-3,3- (2,2-dimethyltrimethylenedioxy)-androstan-17-one by 1) 11β, 19-(4-trifluoromethylsulfonyloxy-o-phenylene)-9α-hydroxy-4-androstene-3,17-dione[4], 2) 11β, 19-(4-trifluoromethylsulfonyloxy-o-phenylene)-4,8-androstadiene-3,17-dione[5], 3) 3-ethoxy-11β, 19-(4-trifluoromethylsulfonyloxy-ophenylene)-3,5,8-androstatrien-17-one and 4) 3-ethoxy-17α-(prop-1-inyl)-11β, 19-(4-trifluoromethylsulfonyloxy-o-phenylene)-3,5,8-androstatrien-17β-ol.

$^1$H-NMR (CDCl$_3$) [δ]ppm: 7.44 (1H, d J=8 Hz); 7.11 (1H, dd J=8 Hz and J$_1$=2 Hz); 6.96 (1H d J$_1$=2 Hz); 5.92 (1H, s); 3.74 (1H, m); 3.15 (1H, d J=17.5 Hz); 2.99 (1H, d J=17.5 Hz); 1.9 (3H, ss); 0.5 (3H, s)

[4] $^1$H-NMR (CDCl$_3$) [δ]ppm: 7.52 (1H, d J=8.5 Hz); 7.12 (1H, dd J=8.5 Hz and J$_1$=2 Hz); 7.06 (1H d J$_1$=2 Hz); 6.02 (1H, s); 3.5 (1H, d J=17.5 Hz); 3.2 (1H, d J=5 Hz); 2.96 (1H, d J=17.5 Hz); 0.34 (3H, s)

[5] $^1$H-NMR (CDC13) [δ]ppm: 7.42 ( 1H, d J=8.5 Hz ); 7.13 ( 1H, dd J=8.5 Hz and J$_1$=2 Hz); 7.96 (1H d J$_1$1=2 Hz); 5.95 (1H, s); 3.77 (1H, m); 3.15 (1H, d J=17.5 Hz); 2.99 (1H, d J=17.5 Hz); 0.58 (3H, s)

b) 17β-Hydroxy-17α-(prop-1-inyl)-11β, 19-(4-tri-n-butyl-stannyl-o-phenylene)-4,8-androstadien-3-one 3.5 g of the triflate produced in a) is dissolved in 225 ml of absolute dioxane and mixed with 1 g of lithium chloride and 480 mg of tetrakistriphenylphosphinepalladium. After five minutes more of stirring the reaction mixture is mixed with 12 ml of hexa-n-butylditin, refluxed under protective gas for 2.5 hours, cooled to room temperature and diluted with ethyl acetate. After filtration on Celite and washing of the filter residue with ethyl acetate the organic phase is washed with saturated sodium chloride solution, dried on sodium sulfate and concentrated by evaporation in a vacuum. Chromatography of the residue on silica gel with a mixture of ethyl acetate/hexane yields 2.86 g of 178-hydroxy-17α-(prop-1-inyl)-11β, 19-(4-tri-n-butylstannyl-o-phenylene)-4,8-androstadien-3-one as yellowish foam.

$^1$H-NMR (CDCl$_3$) [δ]ppm: 7.28 (2H, s); 7.06 (1H, s); 5.89 (1H, s); 3.73 (1H, m); 3.13 (1H, d J=17.5 Hz); 2.95 (1H, d J=17.5 Hz); 1.9 (3H, ss); 0.87 (9H, tr J=7.5 Hz); 0.53 (3H, s)

c) 17β-Hydroxy-17α-(prop-1-inyl)-11β, 19-[4-(5-pyrimidinyl)-o-phenylene]-4,8-androststadien-3-one 2.8 g of the tin compound produced in b) is dissolved in 100 ml of absolute toluene and mixed with 6.48 g of 5-bromopyrimidine and 110 mg of tetrakistriphenylphosphinepalladium and the reaction mixture is refluxed for 14 hours. Then it is cooled to room temperature, concentrated by evaporation in a vacuum and the residue is chromatographed on silica gel with a mixture of ethyl acetate/hexane. 1.35 g of the title compound is isolated as yellowish foam.

$^1$H-NMR (CDCl$_3$) [δ]ppm: 9.2 (1H, s); 8.95 (2H, s); 7.4–7.72 (3H, m); 5.93 (1H, s); 3.83 (1H, d broad J=7.5 Hz); 3.22 (1H, d J=17.5 Hz); 3.07 (1H, d J=17.5 Hz); 1.93 (3H, s); 0.57 (3H, s)

EXAMPLE 8

17β-Hydroxy-17α-(3-hydroxyprop-1-inyl)-11β, 19-[4-(3-pyridyl)-o-phenylene], 4,8-androstadien-3-one a) 17β-Hydroxy-17α-(3-hydroxyprop-1-inyl)-11β, 19-(4-trifluoromethylsulfonyloxy-o-phenylene)-4,8-androstadien-3-one Analogously to example 6 a) or example 1, by addition of 3-(tetrahydropyran-2-yloxy)-prop-1-ine (see example 5) instead of prop-1-ine, 5.66 g of 17β-hydroxy-17α-(3-hydroxyprop-1-inyl)-11β, 19-(4-trifluoromethylsulfonyloxy-o-phenylene)-4,8-androstadien-3-one is obtained as yellowish foam starting from 10 g of 11β, 19-4-trifluoromethylsulfonyloxy-o-phenylene)-4,8-androstadiene-3,17-dione.

$^1$H-NMR (CDCl$_3$) [δ]ppm: 7.44 (1H, d J=8.5 Hz); 7.12 (1H, d J=8.5 Hz and Jl=2 Hz); 6.96 (1H, d J=2 Hz); 5.91 (1H, s); 4.37 (2H, s); 3.84 (3H, s); 3.77 (1H, m); 3.16 (1H, d J=17.5 Hz); 3.0 (1H, d J=17.5 Hz); 0.52 (3H, s)

b) 17β-Hydroxy-17α-(3-hydroxyprop-1-inyl)-11β, 19-[4-(3-pyridyl)-o-phenylene]-4,8-androstadien-3-one 1 g of the triflate produced in a) is dissolved in a mixture of 20 ml of toluene and 10 ml of ethanol and mixed in succession with 110 mg of palladiumtetrakistriphenylphosphine, 155 mg of lithium chloride, 2.5 ml of 2 m sodium carbonate solution and 290 mg of diethyl-(3-pyridyl)-borane. The reaction mixture is then stirred for 1 hour at 110° C., cooled to room temperature and mixed with saturated sodium chloride solution. The organic phase is separated, washed in succession with 5% sodium hydroxide solution and water, washed by sodium sulfate and concentrated by evaporation in a vacuum. The residue is chromatographed on silica gel with a mixture of ethyl acetate/hexane. 640 mg of the title compound is obtained as yellowish foam.

$^1$H-NMR (CDCl$_3$) [δ]ppm: 8.83 (1H, s broad); 8.57 (1H, dd J$_1$=2 and J$_2$=5 Hz); 7.89 (1H, dtr J$_1$=2 and J$_2$=7.5 Hz); 7.33–7.52 (3H, m); 7.26 (1H, s broad); 5.91 (1H, s); 4.34 (2H, d J=5 Hz); 3.8 (1H, d broad J=7.5 Hz); 3.21 (1H, d J=17.5 Hz); 3.06 (1H, d J=17.5 Hz); 0.57 (3H, s)

EXAMPLE 9

17-Hydroxy-17α-(3-hydroxyprop-1-inyl)-11β, 19-[4-(4-methoxyphenyl)-o-phenylene]-4,8-androstadien-3-one Analogous to the coupling instructions described in example 8 b) 1 g of the triflate produced in 8 a) is reacted with 300 mg of 4-methoxyphenylboronic acid to 491 mg of the title compound.

$^1$H-NMR (CDCl$_3$) [δ]ppm: 7.51 (2H, d J=8.5 Hz); 7.36–7.46 (2H, m); 7.22 (1H, s broad); 6.97 (2H, d J=8.5 Hz); 5.92 (1H, s); 4.39 (2H, d J=5 Hz); 3.84 (3H, s) ; 3.79 (1H, d broad J=7.5 Hz); 3.18 (1H, d J=17.5 Hz); 3.04 (1H, d J=17.5 Hz); 0.59 (3H, s)

EXAMPLE 10

17β-Hydroxy-17α,(3-hydroxyprop-1-inyl)-11β, 19-[4-(4-methylthiophenyl)-o-phenylene]-4,8-androstadien-3-one Analogous to the coupling instructions described in example 8b) 1 g of the triflate produced in 8a) is reacted with 330 mg of 4-methoxythiophenylboronic acid to 567 mg of the title compound.

$^1$H-NMR (CDCl$_3$) [δ]ppm: 7.51 (2H, d J=8.5 Hz); 7.37–7.47 (2H, m); 7.3 (2H, d J=8.5 Hz); 7.24 (1H, s broad); 5.92 (1H, s); 4.4 (2H, s); 3.8 (1H, d broad J=7.5 Hz); 3.18 (1H, d J=17.5 Hz); 3.04 (1H, d J=17.5 Hz), 2.52 (3H, s); 0.57 (3H, s)

EXAMPLE 11

11β, 19-(4-Acetyl-o-phenylene)-17β-hydroxy-17α-(3-hydroxyprop-1-inyl)-4,8-androstadien-3-one 1 g of the triflate produced in example 8a) is dissolved in 15 ml of absolute dimethylformamide and mixed with 150 mg of lithium chloride and 55 mg of tetrakistriphenylphosphinepalladium. After 5 minutes more stirring the reaction mixture is mixed with 0.8 ml of (1-ethoxyvinyl)-tri-n-butyl tin, stirred under protective gas for 15 hours at 110° C. cooled to room temperature and stirred in 1 n aqueous hydrochloric acid solution. The aqueous phase is extracted several times with ethyl acetate. The combined organic phases are washed neutral with saturated sodium bicarbonate solution and saturated sodium chloride solution, dried on sodium sulfate and concentrated by evaporation in a vacuum. Chromatography of the residue on silica gel with a mixture of ethyl acetate/hexane yields 489 mg of the title compound as yellowish foam.

$^1$H-NMR (CDCl$_3$) [δ]ppm: 7.79 (1H, d J=8.5 Hz); 7.65 (1H, s); 7.47 (1H, d J=8.5 Hz); 5.92 (1H, s); 4.38 (2H, s); 3.8 (1H, d broad J=7.5 Hz); 3.18 (1H, d 17.5 Hz); 3.05 (1H, d J=17.5 Hz); 2.59 (3H, s); 0.53 (3H, s)

EXAMPLE 12

17 β-Hydroxy- 17α-(3-hydroxyprop-1(Z) -enyl)-11β, 19-[4-(3)-o-phenylene]-4,8-androstadien-3-one Analogous to the reaction instructions described in example 6, 350 mg of the acetylene obtained in example 8b) is hydrogenated. After chromatography on silica gel with a mixture of ethyl acetate/hexane 295 mg of the title compound is isolated as yellowish foam.

$^1$H-NMR (CDCl$_3$) [δ]ppm: 8.82 (1H, s broad); 8.54 (1H, dd J$_1$=2 and J$_2$=5 Hz); 7.88 (1H, dtr J$_1$=2 and J$_2$=7.5 Hz); 7.32–7.51 (3H, m); 7.25 (1H, s broad); 5.9 (1H, s); 5.7–5.84 (2H, m); 4.32–4.42 (2H, m); 3.79 (1H,d broad J=7.5 Hz); 3.21 (1H, d J=17.5 Hz); 3.06 (1H, d J=17.5 Hz); 0.65 (3H, s)

EXAMPLE 13

17β-Hydroxy-17α-(3-hydroxyprop-1 (Z) -enyl)-11β, 19-[4-(4-methoxyphenyl)-o-phenylene]-4,8-androstadien-3-one Analogous to the reaction instructions described in example 6, 250 mg of the acetylene obtained in example 9 is hydrogenated. After chromatography on silica gel with a mixture of ethyl acetate/hexane 175 mg of the title compound is isolated as yellowish foam.

$^1$H-NMR (CDCl$_3$) [δ]ppm: 7.52 (2H, d J=8.5 Hz); 7.35–7.45 (2H, m); 7.22 (1H, s broad); 6.98 (2H, d J=8.5 Hz); 5.91 (1H, s); 5.69–5.82 (2H, m); 4.33–4.44 (2H, m) ; 3.85 (3H, s) ; 3.78 (1H, d broad J=7.5 Hz); 3.18 (1H, d J=17.5 Hz); 3.04 (1H, d J=17.5 Hz); 0.67 (3H, s);

EXAMPLE 14

17β-Hydroxy- 17α-(3-hydroxyprop-1(Z)-enyl)-11β, 19-[4-(4-methylthipheny-1)-o-phenylene]-4,8-androstadien-3-on.

Analogous to the reaction instructions described in example 6, 310 mg of the acetylene obtained in example 10 is hydrogenated. After chromatography on silica gel with a mixture of ethyl acetate/hexane 265 mg of the title compound is isolated as yellowish foam.

$^1$H-NMR (CDCl$_3$) [δ]ppm: 7.51 (2H, d J=8.5 Hz); 7.37–7.47 (2H, m); 7.3 (2H, d J=8.5 Hz); 7.24 (1H, s broad); 5.91 (1H, s); 5.7–5.85 (2H, m); 4.32–4.43 (2H, m); 3.8 (1H, d broad J=7.5 Hz); 3.17 (1H, d J=17.5 Hz); 3.03 (1H, d J=17.5 Hz); 2.51 (3H, s); 0.68 (3H, s)

EXAMPLE 15

11β, 19-(4-acetyl-o-phenylene)-17β-hydroxy-17-(3-hydroxyprop-1(Z)-enyl)-4,8-androstadien-3-one Analogous to the reaction instructions described in example 6, 275 mg of the acetylene obtained in example 11 is hydrogenated. After chromatography on silica gel with a mixture of ethyl acetate/hexane 215 mg of the title compound is isolated as yellowish foam.

¹H-NMR (CDCl₃) [δ]ppm: 7.8 (1H, d J=8.5 Hz); 7.66 (1H, s); 7.48 (1H, d J=8.5 Hz); 5.91 (1H, s); 5.69–5.73 (2H, m); 4.32–4.42 (2H, m); 3.8 (1H, d broad J=7.5 Hz); 3.18 (1H, d J=17.5 Hz); 3.05 (1H, d J=17.5 Hz); 2.6 (3H, s); 0.59 (3H, s)

EXAMPLE 16

11β, 19-(4-Acetyl-o-phenylene)-17β-hydroxy-17α -(prop-1-inyl)-4,8-androstadien-3-one a) 11β, 19-(4-Nonafluorobutylsulfonyloxy-o-phenylene)-3,3-(2,2-dimethyltrimethylenedioxy)-androstane-5α,9α,17β-triol 22.5 g of 11β, 19-(4-hydroxy-o-phenylene)-3,3-(2,2-dimethyltrimethylenedioxy)-androstane-5α, 9α, 17β-triol is introduced in 720 ml of absolute tetrahydrofuran at 0° C. and mixed with 29 ml of 1.6 molar n-butyllithium solution (hexane). After 30 more minutes stirring 9.2 ml of nonafluorobutylsulfonyl fluoride is instilled. Finally the reaction mixture is slowly heated over 1.5 hours to 15° C. and then poured in saturated sodium bicarbonate solution. After 45 more minutes of stirring the aqueous phase is extracted several times with ethyl acetate. The combined organic phases are washed with saturated sodium chloride solution, dried on sodium sulfate and concentrated by evaporation in a vacuum. 35.6 g of the title compound is obtained as crude product.

After chromatography of 500 mg of the crude product on silica gel with a mixture of ethyl acetate/hexane 384 mg of 11β, 19-(4-nonafluorobutylsulfonyloxy-o-phenylene)-3,3-(2,2-dimethyltrimethylenedioxy)-androstane-5α, 9α, 17β-triol is isolated as white foam.

Melting point: 181°–182° C. (diisopropylether)
[α]²⁰_D=26° (CHCl₃; c=0.52)

b) 11β, 19-(4-Nonafluorobutylsulfonyloxy-o-phenylene)-5α,9α-dihydroxy-3,3-(2,2-dimethyltrimethylenedioxy)-androstan-17-one 25.4 g of chromiumtrioxide is added in portions at 0° C. to a mixture of 85 ml of pyridine and 250 ml of methylene chloride. Then 35.1 g of the compound produced in a), dissolved in 100 ml of methylene chloride, is slowly instilled at the same temperature and the reaction mixture stirred overnight under slow heating to room temperature. After completion of the stirring the solid components are allowed to settle, the supernatant phase is decanted and the precipitate is thoroughly washed several times with methylene chloride. The combined organic phases are freed of residual inorganic components by washing with 0.5 m potassium hydroxide solution, washed neutral with water, dried on sodium sulfate and concentrated by evaporation in a vacuum. 19.6 g of the title compound is obtained by chromatography of the residue on aluminum oxide (neutral, step III) with a mixture of ethyl acetate/hexane.

Melting point: 175°–176° C. (ethyl acetate)
[α]²⁰_D=35° (CHCl₃; c=0.535)

c) 17β-Hydroxy-11β, 19-(4-nonafluorobutylsulfonyloxy-o-phenylene)-17α-(prop-1-inyl)-4,8-androstadien-3-one In an analogous sequence to the reaction instructions described in example 1, 3.75 g of 17β-hydroxy-11β, 19-(4-nonafluorobutylsulfonyloxy-o-phenylene)-17α-(prop-1-inyl)-4,8-androstadien-3-one is produced as white foam starting from 9.5 g of 11β, 19-(4-nonafluorobutylsulfonyloxy-o-phenylene)-5α, 9α-dihydroxy-3,3-(2,2-dimethyltrimethylenedioxy)-androstan-17-one by 1) 11β, 19-(4-nonafluorobutylsulfonyloxy-o-phenylene)-9α-hydroxy-4-androstene,3,17-dione[6], 2) 11β, 19-(4-nonafluorobutylsulfonyloxy-o-phenylene)-4,8-androstadiene-3,17-dione[7], 3) 3-ethoxy-11β, 19-(4-nonafluorobutylsulfonyloxy-o-phenylene)-3,5,8-androstatrien-17-one and 4) 3-ethoxy-17α-(prop-1-inyl)-11β, 19-(4-nonafluorobutylsulfonyloxy-o-phenylene)-3,5,8-androstatrien-17β-ol.

¹H-NMR (CDCl₃) [δ]ppm: 7.44 (1H, d J=9 Hz); 7.13 (1H, dd J=9 Hz and J₁=2 Hz ); 6.97 (1H, d J₁=2 Hz); 5.93 (1H, s); 3.76 (1H, m); 3.17 (1H, J=17.5 Hz); 3.0 (1H, d J=17.5 Hz); 1.9 (3H, s); 0.5 (3H, s)

[6] ¹H-NMR (CDCl₃) [δ]ppm: 7.52 (1H, d J=8.5 Hz); 7.13 (1H, dd J=8.5 Hz and J₁=2 Hz); 7.07 (1H, d J₁=2 Hz); 6.06 (1H, s); 3.51 (1H, d J=17.5 Hz; 3.2 (1H, d J=5 Hz); 2.98 (1H, d J=17.5 Hz); 0.33 (3H, s)

[7] ¹H-NMR (CDCl₃) [δ]ppm: 7.42 (1H, d J=8.5 Hz); 7.14 (1H, dd J=8.5 Hz and J₁=2 Hz); 7.97 (1H, d J₁=32 2 Hz); 5.95 (1H, s); 3.77 (1H, m); 3.15 (1H, d J=17.5 Hz); 2.99 (1H, d J=17.5 Hz); 0.59 (3H, s)

d) 11β, 19-(4-Acetyl-o-phenylene)-17β-hydroxy-17-(prop-1-inyl)-4,8-androstadien-3-one Analogous to the reaction instructions described in example 11, 850 mg of the acetylene obtained in c) is coupled in 10 ml of absolute dioxane. After concentration by evaporation of the reaction mixture and chromatography of the residue on silica gel with a mixture of ethyl acetate/hexane 264 mg of the title compound is isolated as white foam.

¹H-NMR (CDCl₃) [δ]ppm: 7.8 (1H, d J=8.5 Hz); 7.65 (1H, s); 7.48 (1H, d J=8.5 Hz); 5.93 (1H, s); 3.8 (1H, d broad J=7.5 Hz); 3.18 (1H, d J=17.5 Hz); 3.05(1H, d J=17.5 Hz); 2.6 (3H, s); 1.92 (3H, s); 0.5 (3H, s)

EXAMPLE 17

17β-Hydroxy-11β, 19-[4-(4-methylthiophenyl)-o-phenylene]-17α (prop-1-inyl)-4,8-androstadien-3-one Analogous to the reaction instructions described in example 8 b), 700 mg of the acetylene obtained in example 16 c) is coupled with 185 mg of 4-methylthiophenylboronic acid. After concentration by evaporation of the reaction mixture and chromatography of the residue on silica gel with a mixture of ethyl acetate/hexane 322 mg of the title compound is isolated as yellowish foam.

¹H-NMR (CDCl₃) [δ]ppm: 7.51 (1H, d J=8.5 Hz); 7.42 (1H, s); 7.31 (1H, d J=8.5 Hz); 5.92 (1H, s); 3.79 (1H, m); 3.18 (1H, d J=17.5 Hz); 3.03 (1H, d J=17.5 Hz); 2.51 (3H, s); 1.92 (3H, s); 0.57 (3H, s)

EXAMPLE 18

17β-Hydroxy-11β, 19-[4-(3-furanyl)-o-phenylene]-17α-(prop-1-inyl)-4,8-androstadien-3-one Analogous to the reaction instructions described in example 8 b), 700 mg of the acetylene obtained in example 16 c) is coupled with 0.5 ml of ( 3 -furanyl ) -tributylstannane. After concentration by evaporation of the reaction mixture and chromatography of the residue on silica gel with a mixture of ethyl acetate/hexane 395 mg of the title compound is isolated as yellowish foam.

¹H-NMR (CDCl₃) [δ]ppm: 7.7 (1H, s); 7.48 (1H, tr J=1Hz); 7.36 (2H, m); 7.15 (1H, s); 6.69 (1H, m); 5.92 (1H, s); 3.77 (1H, m broad); 3.15 ( 1H, d J=17.5 Hz ); 3.0 ( 1H, d J=17.5 Hz ); 1.9 ( 3H, s); 0.57 (3H, s)

EXAMPLE 19

17β-Hydroxy-17α-(prop-1-inyl)-11β, 19-[4-(3-pyridinyl)-ophenylene]-4,8-androstadien-3-one Analogous to the reaction instructions described in example 8 b), 500 mg of the acetylene obtained in example 16 c) is coupled. After concentration by evaporation of the reaction mixture and chromatography of the residue on silica gel with a mixture of ethyl acetate/hexane 284 mg of the title compound is isolated as yellowish foam.

¹H-NMR (CDCl₃) [δ]ppm: 8.83 (1H, s broad); 8.58 (1H, dd J₁=2 and J₂=5 Hz); 7.89 (1H, dtr Jl=2 and J₂=7.5 Hz); 7.3–7.7 (4H, m); 5.92 (1H, s); 3.8 (1H, d broad J=6.5 Hz); 3.2 (1H, d J=16.5 Hz); 3.05 (1H, d J=16.5 Hz); 1.91 (3H, s); 0.57 (3H, s)

EXAMPLE 20

17β-Hydroxy-17α-methyl-11β, 19-[4-(4-cyanophenyl)-ophenylene]-4,8-androstadien-3-one a) 17β-Hydroxy-17α-methyl-11β, 19-(4-hydroxy-o-phenylene)-4,8-androstadien-3-one 50 ml of a 1.6 m methyllithium solution (diethylether) is introduced under protective gas and 9 g of 3-ethoxy-11β, 19-(4-nonafluorobutylsulfonyloxy-o-phenylene)-3,5,8-androstatrien-17-one [example 16 c) 3)]dissolved in 80 ml of absolute diethylether is instilled. After 10 minutes of stirring the ice-cold reaction mixture is poured on saturated sodium bicarbonate solution and the aqueous phase extracted with ethyl acetate. The combined organic phases are washed with saturated sodium chloride solution, dried on sodium sulfate and concentrated by evaporation in a vacuum. The residue is taken up in a mixture of 225 ml of acetone and 5 ml of 4 n aqueous hydrochloric acid and stirred for 1 hour at room temperature. Then the reaction mixture is poured on saturated sodium bicarbonate solution and the aqueous phase extracted with ethyl acetate. The combined organic phases are washed with saturated sodium chloride solution, dried on sodium sulfate and concentrated by evaporation in a vacuum. The residue is chromatographed on silica gel with a mixture of ethyl acetate/hexane. 1.65 g of the title compound and 0.56 g of 11β, 19-(4-hydroxy-o-phenylene)-4,8-androstadiene-3,17-dione[8] are isolated.

¹H-NMR (CDCl₃) [δ]ppm: 7.19 (1H, d J=8.5 Hz); 6.69 (1H, dd J=8.5 and J₁=2 Hz); 6.49 (1H, d J=2 Hz); 6.1 (1H, s); 5.93 (1H, s); 3.66 (1H, m broad); 3.09 (1H, d J=17.5 Hz); 2.88 (1H, d J=17.5 Hz); 1.31 (3H, s); 0.54 (3H, s) [8] ¹H-NMR (CDCl₃) [δ]ppm: 7.19 (1H, d J=8.5 Hz); 6.72 (1H, dd J=8.5 and Jl=2 Hz); 6.5 (1H, d J=2 Hz); 5.94 (1H, s); 5.59 (1H, s); 3.69 (1H, m broad); 3.08 (1H, d J=17.5 Hz); 2.88 (1H, d J=17.5 Hz); 0.6 (3H, s)

b) 17β-Hydroxy-17α-methyl-11β, 19-(4-trifluoromethylsulfonyloxy-o-phenylene)-4,8-androstadien-3-one 1.5 g of the methyl compound obtained in a) is dissolved in 75 ml of absolute methylene chloride and mixed with 3.63 g of 4-dimethylaminopyridine. The solution is then cooled to −78° C. under protective gas and mixed by slow instillation with 1.05 ml of trifluoromethanesulfonic acid anhydride dissolved in 10 ml of absolute methylene chloride. After 4 more hours of stirring at −70° C. the reaction mixture is carefully poured on saturated sodium bicarbonate solution and the aqueous phase is extracted with methylene chloride. The combined organic phases are washed with saturated sodium chloride solution, dried on sodium sulfate and concentrated by evaporation in a vacuum. The residue is chromatographed on silica gel with a mixture of ethyl acetate/ hexane. 1.69 g of the title compound is isolated.

¹H-NMR (CDCl₃) [δ]ppm: 7.43 (1H, d J=9 Hz); 7.11 (1H, dd J=9 Hz and J₁=2 Hz); 6.95 (1H, d Jl=2 Hz); 5.92 (1H, s) ; 3.73 (1H, m); 3.17 (1H, d J=17.5 Hz); 3.01 (1H, d J=17.5 Hz); 1.32 (3H, s); 0.52 (3H, s)

c) 17β-Hydroxy-17α-methyl-11β, 19-[4-(4-cyanophenyl)-o-phenylene]-4,8-androstadien-3-one 800 mg of the triflate produced in b) is coupled with 350 mg of 4-cyanophenylboronic acid[9] analogously to the reaction instructions described in example 8 b). After concentration by evaporation of the reaction mixture and chromatography of the residue on silica gel with a mixture of ethyl acetate/hexane 552 mg of the title compound is isolated as white foam.

¹H-NMR (CDCl₃) [δ]ppm: 7.65–7.77 (4H, m); 7.4–7.52 (2H, m); 7.28 (1H d J₁=2 Hz); 5.93 (1H, s); 3.79 (1H, m); 3.21 (1H, d J=17.5 Hz); 3.06 (1H, d J=17.5 Hz); 1.34 (3H, s); 0.55 (3H, s)

9 S. Takahashi et al. Bull. Chem. Soc. Jpn. 62, 3896 (1989)

EXAMPLE 21

17α-Cyanomethyl-17β-hydroxy-11β, 19-[4-(4-cyanophenyl)-o-phenylene]-4,8-androstadien-3-one a) 17α-Cyanomethyl-17β-hydroxy-11β, 19-(4-hydroxy-o-phenylene)-4,8-androstadien-3-one 17.4 ml of diisopropylamine is introduced in 250 ml of absolute tetrahydrofuran under protective gas and mixed with 77.5 ml of 1.6 m n-butyllithium solution (hexane) at −30° C. The solution is stirred for 30 minutes at 0° C. for complete deprotonization, before it is cooled down to −70° C. After instillation of 6.52 ml of acetonitrile it is stirred for one hour at −70° C. Then 8 g (crude product) of 3-ethoxy-11β, 19-(4-trifluoromethylsulfonyloxy-o-phenylene)-3,5,8-androstatrien-17-one [example 7 a) 3)]dissolved in 65 ml of absolute tetrahydrofuran is slowly instilled. After 60 minutes of stirring the reaction mixture is poured on saturated sodium bicarbonate solution and the aqueous phase is extracted with saturated ethyl acetate. The combined organic phases are washed with saturated sodium chloride solution, dried on sodium sulfate and concentrated by evaporation in a vacuum. The residue is taken up in a mixture of 300 ml acetone and 5 ml of 4n aqueous hydrochloric acid and stirred for one hour at room temperature. Then the reaction mixture is poured on saturated sodium bicarbonate solution and the aqueous phase is extracted with ethyl acetate. The combined organic phases are washed with saturated sodium chloride solution, dried on sodium sulfate and concentrated by evaporation in a vacuum. The residue is chromatographed on silica gel with a mixture of ethyl acetate/hexane. 3.25 g of the title compound is isolated.

$^1$H-NMR (CDCl$_3$) [δ]ppm: 7.19 (1H, d J=8.5 Hz); 6.7 (1H, dd J=8.5 and J$_1$=2 Hz); 6.5 (1H, d J=2 Hz); 5.91 (1H, s); 5.59 (1H, s broad); 3.71 (1H, m broad); 3.8 (1H, d J=17.5 Hz); 2.9 (1H, d J=17.5 Hz); 2.72 (1H, d J=17.5 Hz); 2.57 (1H, d J=17.5 Hz); 0.59 (3H, s)

b) 17α-Cyanomethyl-17β-hydroxy-11β, 19-(4-trifluoromethylsulfonyloxy-o-phenylene)-4,8-androstadien-3-one 3.1 g of the cyanomethyl compound obtained in a) is dissolved in 140 ml of absolute methylene chloride and mixed with 6.7 g of 4-dimethylaminopyridine. The solution is then cooled to −78° C. under protective gas and mixed by slow instillation with 1.96 ml of trifluoromethanesulfonic acid anhydride dissolved in 20 ml of absolute methylene chloride. After 5 hours of stirring at −70° C. the reaction mixture is carefully poured on saturated sodium bicarbonate solution and the aqueous phase is extracted with methylene chloride. The combined organic phases are washed with saturated sodium chloride solution, dried on sodium sulfate and concentrated by evaporation in a vacuum. The residue is chromatographed on silica gel with a mixture of ethyl acetate/hexane. 2.75 of the title compound is isolated.

$^1$H-NMR (CDCl$_3$) [δ]ppm: 7.45 (1H, d J=9 Hz); 7.12 (1H, dd J=9 Hz and J$_1$=2 Hz); 6.98 (1H, d J$_1$=2 Hz); 5.93 (1H, s); 3.78 (1H, m); 3.17 (1H, d J=17.5 Hz); 3.03 (1H, d J=17.5 Hz); 2.73 (1H, d J=17.5 Hz); 2.58 (1H, d J=17.5 Hz); 0.56 (3H, s)

c) 17α-Cyanomethyl-17β-hydroxy-11β, 19-[4-(4-cyanophenyl-ophenylene]-4,8-androstadien-3-one 1 g of the triflate produced in b) is coupled with 350 mg of 4-cyanophenylboronic acid analogously to the reaction instructions described in example 8 b). After concentration by evaporation of the reaction mixture and chromatography of the residue on silica gel with a mixture of ethyl acetate/hexane 552 mg of the title compound is isolated as white foam.

Melting point: 212°–213° C. (ethyl acetate)
[α]$^{20}_D$=224° (CHCl$_3$; c=0.51)

EXAMPLE 22

17α-Cyanomethyl-17β-hydroxy-11β, 19-[4-(4-dimethylarainophenyl)-o-phenylene]-4,8-androstadien-3-one 1 g of the triflate produced in example 21 b) is coupled with 330 mg of 4-dimethylaminophenylboronic acid[10] analogously to the reaction instructions described in example 8 b). After concentration by evaporation of the reaction mixture and chromatography of the residue on silica gel with a mixture of ethyl acetate/hexane 460 mg of the title compound is isolated as yellowish foam.

[10]H.Staab et al. Liebigs Ann. Chem. 753, 80 (1971)
Melting point: 289°–290° C. (ethyl acetate)
[α]$^{20}_D$=226° (CDCl$_3$; c=0.51)

We claim:
1. A 8-en-19, 11β-bridged steroid compound of formula I

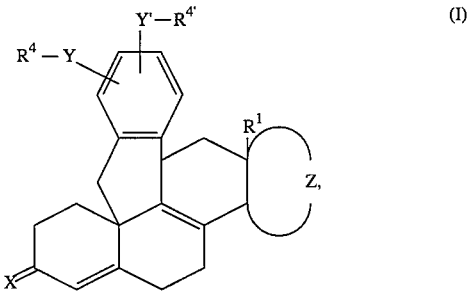

wherein
R$^1$ is methyl or ethyl;
X is an oxygen atom, a hydroxyimino group or two hydrogen atoms;
Z is a ring of formula

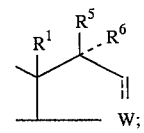

wherein
———is a single bond or a double bond;
W is —CH$_2$—, =CH—, —CH$_2$CH$_2$— or =CHCH$_2$—;
R$^5$ and R$^6$ are, respectively,
—OR$^7$ and —C≡C—U, —OR$_7$ and

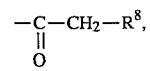

and —OR$^7$,

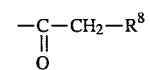

and —CH$_3$,

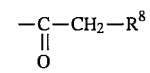

and —H, —OR$^7$ and —(CH$_2$)$_m$—CH$_2$—R$^9$, —OR$^7$ and —CH=CH(CH$_2$)$_k$—CH$_2$—R$^9$ or —R$^{10}$ and —(CH$_2$)$_k$—C≡C—U, or $R^5$ and $R^6$, together, are

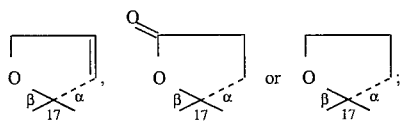

$R^7$ is hydrogen, alkyl having 1–4 C atoms, or acyl having 1–4 C atoms;

U is hydrogen, alkyl having 1–4 C atoms, hydroxyalkyl having 1–4 C atoms, alkoxyalkyl having 1–4 C atoms in each alkyl portion, acyloxyalkyl having 1–4 C atoms in each of the alkyl and acyl portions, or a halogen atom;

$R^8$ is hydrogen, hydroxy, alkyl having 1–4 C atoms, O-alkyl having 1–4 C atoms, or O-acyl having 1–4 C atoms;

$R^9$ is hydrogen, hydroxy or cyano, O-alkyl having 1–4 C atoms, or O-acyl having 1–4 C atoms;

$R^{10}$ is hydrogen, alkyl having 1–10 C atoms or acyl having 1–10 C atoms, m is 0, 1, 2 or 3;

k is 0, 1 or 2;

$R^4$ and $R^{4'}$, being the same or different, are each hydrogen, cyano, $-OR^{11}$, $-S(O)_k R^{11}$, $-N(O)_n R^{11} R^{12}$, $-O-SO_2-R^{13}$, $-P(O)(OR^{14})_2$, $-SiR_3^{14}$ or $-SnR_3^{14}$;

k is 0, 1 or 2;

n is 0 or 1;

$R^{11}$ is hydrogen or $C_1-C_8$-alkyl;

$R^{12}$ is H, $C_1-C_8$-alkyl, cyano, $C_1-C_{10}$-acyl;

$R^{13}$ is a perfluorinated $C_1-C_4$-alkyl radical;

$R^{14}$ is $C_1-C_4$-alkyl; or $R^{11}$ and $R^{12}$ within a $-N(O)_n R^{11} R^{12}$ group can also together, with the inclusion of N, form a 5 or 6 membered heterocyclic ring optionally containing another heteroatom selected from N, O and S;

Y and Y', being the same or different, are each a direct bond, a straight-chain or branched alkylene group having up to 20 carbon atoms, optionally containing double and/or triple bond(s) and optionally substituted by one or more oxo-, $C_1-C_{10}$-acyloxy-, $-OR^{11}$, $-S(O)_k R^{11}$ and/or $-N(O)_n R^{11} R^{12}$ group(s), or an aryl radical selected from the group consisting of phenyl, 4-ethylphenyl, naphthyl, 2-methoxyphenyl, 3-methoxyphenyl, 4-methoxyphenyl, 4-vinylphenyl, 4-acetylphenyl, 2-tolyl, 3-tolyl, 4-tolyl, 2-dimethylaminophenyl, 3-dimethylaminophenyl, 4-dimethylaminopbenyl, 2-furyl, 3-furyl, 2-thienyl, 3-thienyl, 2-pyridyl, 3-pyridyl, 4-pyridyl, pyrimidinyl, thiazolyl or imidazolyl;

$R^4$—Y and $R^{4'}$—Y' can also together be an optionally substituted saturated, unsaturated or aromatic 5 or 6 membered ring with 0 to 2 oxygen atoms, sulfur atoms and/or $NR^{11}$-groups;

with the proviso that k and n are greater than 0, only when $R^{11}$ is $C_1-C_8$-alkyl; or a pharmaceutically compatible addition salt thereof with an acid.

2. A compound according to claim 1, wherein Y and Y' are each a direct bond and $R^4$ and $R^{4'}$ are each hydrogen.

3. A compound according to claim 1, wherein Y and Y' are each a direct bond, $R^4$ hydrogen, $R^{4'}$ is $-NR^{11}R^{12}$, and $R^{11}$ and $R^{12}$ are each $C_1-C_8$ alkyl [radicals].

4. A compound according to claim 1, wherein Y and Y' are each a direct bond, $R^4$ is hydrogen and $R^{4'}$ is $C_1C_8$-alkoxy.

5. A compound according to claim 1, wherein Y is a direct bond, $R^4$ and $R^{4'}$ are each hydrogen, and Y' is a straight-chain or branched alkylene group with up to 20 carbon atoms, optionally containing double and/or triple bond(s), and said alkylene group is substituted by an oxo or $OR^{11}$ group 6. [Compounds]A compound according to claim [1]1, wherein $R^4$—Y and $R^{4'}$-Y' together [stand for the radical of] are a saturated, unsaturated or aromatic 5 or 6 membered ring with 0 to 2 oxygen atoms, sulfur atoms and/or $NR^{11}$ groups [with $R^{11}$ meaning a hydrogen atom or a $C_1-C_8$-alkyl radical].

7. A compound according to claim 1, wherein Y'–$R^{4'}$ is hydrogen and Y—$R^4$ is selected from the group consisting of ethyl, vinyl, isopropyl, isopropenyl, prop-1(Z)-enyl, prop-1(E)-enyl, prop-2-enyl, ethinyl, propinyl, prop-2-inyl, methoxy, thiomethyl, thioethyl, 1-hydroxyethyl, diethoxyphosphoryl, [a substituted carbocyclic aryl radical an unsubstituted carbocyclic aryl radical, a substituted heterocyclic aryl radical, or an unsubstituted heterocyclic aryl radical] phenyl, 4-ethylphenyl, naphthyl 2-methoxyphenyl, 3-methoxyphenyl, 4-methoxyphenyl, 4-vinylphenyl, 4-acetylphenyl, 2-tolyl, 3-tolyl, 4-tolyl, 2-dimethylaminophenyl, 3-dimethylaminophenyl, 4-dimethylaminophenyl, 2-furyl, 3-furyl, pyrimidinyl, thiazolyl or imidazolyl.

8. A compound according to claim 1, wherein said aryl radical is selected from the group consisting of phenyl, naphthyl, 2-methoxyphenyl, 3-methoxyphenyl, 4-methoxyphenyl, 2-tolyl, 3-tolyl, 4-tolyl, 2-dimethylaminophenyl 3-dimethylaminophenyl, 4-dimethylaminophenyl, 2-furyl, 3-furyl, 2-thienyl, 3-thienyl, 2-pyridyl, 3-pyridyl, 4-pyridyl, pyrimidinyl, thiazolyl or imidazolyl.

9. A compound according to claim 1, wherein said compound is:

17 β-hydroxy-11β, 19-(4-methoxy-o-phenylene)-17α-(prop-1-inyl )-4,8-androstadien-3-one;

11β, 19-(4-ethylphenyl-o-phenylene)-17β-hydroxy-17α-(prop-1-inyl )-4,8-androstadien-3-one;

11β, 19-[4-(4-cyanophenyl)-o-phenylene]-17β-hydroxy-(prop-1-inyl)-4,8-androstadien-3-one 11β, 19-[4-(4-cyanophenyl)-o-phenylene]-17β-(ethinyl)-17 β-hydroxy-4,8-androstadien-3-one;

11β, 19-[4-(4 -cyanophenyl)-o-phenylene]-17β-hydroxy-17α-(3-hydroxyprop-1-inyl)-4,8-androstadien-3-one;

11β, 19-[4-(4-cyanophenyl)-o-phenylene]-17β-hydroxy-17β-( 3 -hydroxylprop-1(Z)-enyl)-4,8-androstadien-3-one;

17β-hydroxy-17α-(prop-1-inyl) -11β, 19- [4- (5-pyrimidinyl)-o-phenylene]-4,8-androstadien-3-one;

17β-hydroxy-17α-(3-hydroxyprop-1-inyl) -11β, 19-[4-(3-pyridyl)-o-phenylene]-4,8-androstadien-3-one;

17β-hydroxy-17α-(3-hydroxyprop-1-inyl)-11β, 19-[4-(4-methoxyphenyl)-o-phenylene]-4,8-androstadien-3- one;

17β-hydroxy-17α-(3-hydroxyprop-1-inyl)-11β, 19-[4-(4-methylthiophenyl)-o-phenylene]-4,8-androstadien-3-one;

11β, 19-(4-acetyl-o-phenylene)-17β- hydroxy-17α- (3-hydroxyprop-1-inyl)-4,8-androstadien-3-one;

17β-hydroxy-17α-(3-hydroxyprop-1(Z)-enyl)-11β, 19-[4-(3-pyridyl)-o-phenylene]-4,8-androstadien-3-one;

17β-hydroxy-17α-(3-hydroxyprop-1(Z)-enyl)-11β, 19-[4-(4-methoxyphenyl)-o-phenylene]-4,8-androstadien-3-one;

17β-hydroxy-17α-(3-hydroxyprop-1(Z)-enyl)-11β, 19-[4(4-methylthiophenyl)-o-phenylene]-4,8-androstadien-3-one;

11β, 19-(4-acetyl-o-phenylene)-17β-hydroxy-17α-(3-hydroxyprop-1(Z)-enyl)-4,8-androstadien-3-one;

11β, 19-(4-acetyl-o-phenylene)-17β-hydroxy-17α-(prop-1-inyl )-4,8-androstadien-3-one;

17β-hydroxy-11β, 19 -[4-(4-methylthiophenyl)-o-phenylene]-17α-(prop-1-inyl)-4,8-androstadien-3-one;

17β-hydroxy-11β, 19- [4-(3-furanyl)-o-phenylene]-17α-(prop-1-inyl)-4,8-androstadien-3-one;

17β-hydroxy-17α- (prop-1-inyl)-11β, 19-[4-(3-pyridyl)-o-phenylene]-4,8-androstadien-3-one; m); 3.17 (1H, 17β-hydroxy-17α-methyl -11β, 19-[4-(4-cyanophenyl )-o-phenylene]-4,8-androstadien-3-one;

17α-cyanomethyl-17β-hydroxy-11α, 19-[4-(4-cyanophenyl)-o-phenylene]-4,8-androstadien-3-one;

17α-cyanomethyl-17β-hydroxy-11β, 19-[4-(4-dimethylaminophenyl)-o-phenylene]-4,8-androstadien-3-one;

17α-hydroxy-17α-(3-hydroxyprop-1(Z)-enyl)-11β, 19-(4-vinylphenyl-o-phenylene)-4,8-androstadien-3-one;

17β-hydroxy-11β, 19-(4-methylthiophenyl-o-phenylene)-(prop-1-inyl)-4,8-androstadien-3-one;

17β-hydroxy-17α-(3-hydroxyprop-1(Z)-enyl)-11β, 19-(4-methylsulfinylphenyl-o-phenylene)-4,8-androstadien-3-one;

17β-hydroxy-17α-(3-hydroxyprop-1(Z)-enyl)-11β, 19-(4-methylthio-o-phenylene)-4,8-androstadien-3-one;

17β-hydroxy-17α-(3-hydroxyprop-1(Z)-enyl)-11β, 19-(4-methylsulfinyl-o-phenylene)-4,8-androstadien-3-one;

11β19-(4-dimethylamino-o-phenylene)-17β-hydroxy-17α-(3-hydroxylprop-1(Z)-enyl)-4,8-androstadien-3-one;

11β, 19-[4-(4-dimethylaminophenyl)-o-phenylene]-17β-hydroxy-17α-(3-hydroxyprop-1(Z)-enyl)-4,8-androstadien-3-one;

11β, 19-[4-(3-furyl)-o-phenylene]-17β-hydroxy-17α-(3-hydroxylprop-1(Z)-enyl)-4,8-androstadien-3-one;

11β, 19-[4-(4-cyanophenyl)-o-phenylene]spiro[androsta-4,8-diene-17α, 2' (5'H)-furan]-3-one;

11β, 19-[4-(4-cyanophenyl)-o-phenylene]-4', 5'-dihydrospiro[androsta-4,8-diene-17β, 2' (3'H )-furan]-3-one;

11β, 19-[4-(4-acetylphenyl)-o-phenylene]-17β-hydroxy-17α(3-hydroxylprop-1-inyl)-4,8-androstadien-3-one;

11β, 19-[4-(4-acetylphenyl)-o-phenylene]-17β-hydroxy-17α-(3-hydroxylprop-1(Z)-enyl)-4,8-androstadien-3-one;

11β, 19-[4-(4-acetylphenyl)-ophenylene]spiro [androsta-4,8-diene-17β, 2' (5' H)-furan]-3-one;

11β, 19- [4-(4-acetylphenyl)-o-phenylene]-4', 5'-dihydrospiro[androsta-4,8-diene-17β, 2' (3'H)-furan]-3-one;

11β, 19- [4-(4-methylthiophenyl)-ophenylene]spiro [androsta-4,8-diene-17β, 2' (5' H)-furan]-3-one;

11β, 19-[4-(4-methylthiophenyl)-o-phenylene]-4', 5'-dihydrospiro[androsta-4,8-diene-17β, 2' (3'H)-furan]-3-one;

11β, 19-(4-acetyl-o-phenylene)spiro [androsta-4,8-diene-17β, 2' (5'H)-furan]-3-one; or 11β, 19-(4-acetyl-o-phenylene)-4', 5'-dihydrospiro [androsta-4,8-diene-17β, 2' (3'H)-furan]-3-one;

10. A compound according to claim 1, wherein $R^{11}$ is a $C_1$–$C_4$-alkyl group.

11. A compound according to claim 1, wherein $R^{12}$ is formyl, acetyl, propenyl, butyryl or benzoyl.

12. A compound according to claim 1, wherein —N(O)$_n$R$^{11}$R$^{12}$ is pyrrole, pyrrolidine, piperidine, piperazine, morpholine, oxazolidine, thiazolidine, or thiadiazolidine.

13. A compound according to claim 1, wherein $R^6$ is —CH=CH(CH$_2$)$_k$CH$_2$—R$^9$ and k is 0 or 1.

14. A compound according to claim 1, wherein Y and Y', being the same or different, are each a direct bond; a straight-chain or branched alkylene group having up to 20 carbon atoms, optionally containing double and/or triple bond(s) and optionally substituted by one or more oxo-, $C_1$–$C_{10}$-acyloxy-, —OR$^{11}$, —S(O)$_k$R$^{11}$ and/or —N(O)$_n$R$^{11}$R$^{12}$ group(s); phenyl; naphthyl; 2-methoxyphenyl; 3-methoxyphenyl; 4-methoxyphenyl; 2-tolyl; 3-tolyl; 4-tolyl; 2-dimethylaminophenyl; 3-dimethylaminophenyl; 4-dimethylaminophenyl; 2-furyl; 3-furyl; 2-thienyl; 3-thienyl; 2-pyridyl; 3-pyridyl; 4-pyridyl; pyrimidinyl; thiazolyl or imidazolyl.

15. A compound according to claim 1, wherein one of —Y—R$^4$ and —Y'—R$^{4'}$ is H and the other is methoxy, 4-ethylphenyl, 4-cyanophenyl, 5-pyrimidinyl, 3-pyridyl, 4-methoxyphenyl, 4-methylthiophenyl, acetyl, 3-furanyl, 4-dimethylaminophenyl, 4-vinylphenyl, 4-methylsulfinylphenyl, methylthio, methylsulfinyl, dimethylamino, 3-furyl or 4-acetylphenyl.

16. A compound according to claim 1, wherein $R^5$ is hydroxy.

17. A compound according to claim 16, wherein $R^6$ is prop-1-inyl, ethinyl, 3-hydroxyprop-1-inyl, 3-hydroxyprop-1(Z)enyl, methyl or cyanomethyl.

18. A compound according to claim 1, wherein $R^6$ is prop-1-inyl, ethinyl, 3-hydroxyprop-1-inyl, 3-hydroxyprop-1(Z)enyl, methyl or cyanomethyl.

19. A pharmaceutical composition comprising at least one compound according to claim 1, and a pharmaceutically compatible vehicle.

20. A compound of formula III

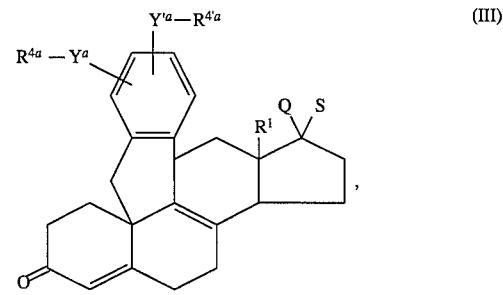

wherein $R^{4a}$ and $R^{4'a}$, being the same or different, are each hydrogen, cyano, —OR$^{11}$, —S(O)$_k$R$^{11}$, —N(O)$_n$R$^{11}$R$^{12}$, —O—SO$_2$—R$^{13}$, —P(O)(OR$^{14}$)$_2$—SiR$_3^{14}$ or —SnR$_3^{14}$;

k is 0, 1 or 2;

n is 0 or 1;

$R^{11}$ is hydrogen or $C_1$–$C_8$-alkyl;

$R^{12}$ is H, $C_1$–$C_8$-alkyl, cyano, $C_1$–$C_{10}$-acyl;

$R^{13}$ is a perfluorinated $C_1$–$C_4$-alkyl radical;

$R^{14}$ is $C_1$≡$C_4$-alkyl;

$R^{11}$ and $R^{12}$ within a —N(O)$_n$R$^{11}$R$^{12}$ group can also together, with the inclusion of N, form a 5 or 6 membered heterocyclic ring, optionally containing another heteroatom selected from N, O and S;

$Y^a$ and $Y'^a$, being the same or different, are each a direct bond, a straight-chain or branched alkylene group having up to 20 carbon atoms, optionally containing double and/or triple bond(s) and optionally substituted by one or more oxo-, $C_1$–$C_{10}$-acyloxy-, —OR$^{11}$, —S(O)$_k$R$^{11}$ and/or —N(O)$_n$R$^{11}$R$^{12}$ group(s), or an [optionally substituted carbocyclic or heterocyclic]aryl radical selected from the group consisting of phenyl, 4-ethylphenyl, naphthyl, 2-methoxyphenyl, 3-methoxyphenyl, 4-methoxyphenyl, 4-vinylphenyl, 4-acetylphenyl, 2-tolyl, 3-tolyl, 4-tolyl, 2-dimethylaminophenyl, 3-dimethylaminophenyl, 4-dimethylaminophenyl, 2-furyl, 3-furyl, 2-thienyl, 3-thienyl 2-pyridyl, 3-pyridyl, 4-pyridyl, pyrimidinyl, thiazolyl or imidazolyl;

with the proviso that k and n are greater than 0 only when $R^{11}$ is $C_1$–$C_8$-alkyl; and optionally any hydroxy, mercapto, amino, oxo and/or terminal acetylene groups present can be in protected form, or $R^{4a}$–$Y^1$— and $R^{4'a}$–$Y'^a$— can each also be methoxy, hydroxy or perfluoroalkylsulfonate;

Q and S together are an oxygen atom or one of the substituent combinations listed in the description of $R^5$ and $R^6$ which will survive a subsequent dehydration reaction step undamaged or in which free hydroxy groups are protected.

* * * * *